US009694090B2

(12) United States Patent
Aime et al.

(10) Patent No.: US 9,694,090 B2
(45) Date of Patent: *Jul. 4, 2017

(54) PROCESS FOR PREPARING HYPERPOLARIZED SUBSTRATES AND METHOD FOR MRI

(75) Inventors: Silvio Aime, Carignano (IT); Giovanni Battista Giovenzana, Novara (IT); Fabio Tedoldi, Pavia (IT); Alessandro Maiocchi, Monza (IT); Fulvio Uggeri, Codogno (IT); Pernille Rose Jensen, Denmark (DK); Magnus Karlsson, Malmo (SE); Mathilde H. Lerche, Frederiksberg C. (DK); Massimo Visigalli, Settala (IT); Marco Crosetti, Turin (IT); Luisa Poggi, Banchette (IT)

(73) Assignee: BRACCO IMAGING S.P.A., Milan (IT)

( * ) Notice: Subject to any disclaimer, the term of this patent is extended or adjusted under 35 U.S.C. 154(b) by 1024 days.

This patent is subject to a terminal disclaimer.

(21) Appl. No.: 13/639,682

(22) PCT Filed: Apr. 8, 2011

(86) PCT No.: PCT/EP2011/055485
§ 371 (c)(1),
(2), (4) Date: Nov. 21, 2012

(87) PCT Pub. No.: WO2011/124672
PCT Pub. Date: Oct. 13, 2011

(65) Prior Publication Data
US 2013/0096420 A1 Apr. 18, 2013

(30) Foreign Application Priority Data
Apr. 8, 2010 (EP) .................... 10159303

(51) Int. Cl.
A61K 49/10 (2006.01)
A61B 5/05 (2006.01)
A61M 5/00 (2006.01)
A61B 5/055 (2006.01)

(52) U.S. Cl.
CPC ............. *A61K 49/10* (2013.01); *A61B 5/055* (2013.01); *A61M 5/007* (2013.01)

(58) Field of Classification Search
CPC ......... A61K 49/10; A61M 5/007; A61B 5/055
See application file for complete search history.

(56) References Cited

U.S. PATENT DOCUMENTS

| 6,466,814 | B1 | 10/2002 | Ardenkjaer-Larsen et al. |
| 2002/0004072 | A1 | 1/2002 | Thomas |
| 2008/0095713 | A1 | 4/2008 | Thaning et al. |
| 2008/0287774 | A1 | 11/2008 | Katz-Brull |
| 2008/0292551 | A1 | 11/2008 | Thaning et al. |
| 2009/0148432 | A1 | 6/2009 | Higuchi |
| 2010/0158810 | A1 | 6/2010 | Lisitza et al. |
| 2010/0190967 | A1 | 7/2010 | Gloegaard et al. |
| 2014/0343402 | A1 | 11/2014 | Aime et al. |

FOREIGN PATENT DOCUMENTS

| EP | 1544634 A1 | 6/2005 |
| JP | 2009527768 A | 7/2009 |
| WO | 88-10419 A1 | 12/1988 |
| WO | 90-00904 A1 | 2/1990 |
| WO | 91-12024 A1 | 8/1991 |
| WO | 93-02711 A1 | 2/1993 |
| WO | 96-39367 A1 | 12/1996 |
| WO | 98-58272 A1 | 12/1998 |
| WO | 99/24080 A1 | 5/1999 |
| WO | 99-35508 A1 | 7/1999 |
| WO | 0196895 A1 | 12/2001 |
| WO | 02-37132 A1 | 5/2002 |
| WO | 2007/044867 A2 | 4/2007 |
| WO | 2007-064226 A2 | 6/2007 |
| WO | 2007-136439 A2 | 11/2007 |
| WO | 2010/037771 A1 | 4/2010 |

OTHER PUBLICATIONS

Jamin et al., Magnetic Resonance in Medicine, 2009, 62, p. 1300-1304.*
"Hydrolysis" http://chem.libretexts.org/Core/Physical_and_Theoretical_Chemistry/Equilibria/Solubilty/Hydrolysis, Oct. 2015.*
Office Action for Japanese application No. 2013-503125, mail date Oct. 7, 2014 (with English language Office Action Summary).
Goldman, Maurice et. al., Design and implementation of 13C hyper polarization from ara-hydrogen, for new MRI contrast agents, Comptes Rendus-Chimie, Elsevier, Paria, FR, vol. 9, No. 3-4, Mar. 1, 2006, pp. 357-363, XP024979705.
Goldman, Maurice et. al., Hyperpolarization of 13C through order transfer from parahydrogen: A new contrast agent for MRI, Magnetic Resonance Imaging, Elsevier Science, Tarrytown, NY, US, vol. 23, No. 2, Feb. 1, 2005, pp. 153-157, XP004843472.
Golman, K. et. al., Molecular imaging using hyperpolarized 13C, The British Journal of Radiology 2003, vol. 76, Spec No. 2, 2003, pp. S118-S127, XP002538147.
Joo, Ferenc, Aqueous biphasic hydrogenations, Accounts of Chemical Research Sep. 2002, vol. 35, No. 9, Sep. 2002, pp. 738-745, XP002538144.
PCT international Search Report for PCT/EP2011/055485, mail date Jun. 30, 2011.
PCT Written Opinion for PCT/EP2011/055485, mail date Jun. 30, 2011.
Reineri, Francesca et. al., New Hyperpolarized contrast agents for 13C MRI from para-hydrogenation of oligooxyethylenic alkynes, Journal of the American Chemical Society 20081112 American Chemical Society US, vol. 130, No. 45, Nov. 12, 2008, pp. 15047-15053, XP002538148.

(Continued)

*Primary Examiner* — Michael G Hartley
*Assistant Examiner* — Leah Schlientz
(74) *Attorney, Agent, or Firm* — Vivicar Law, PLLC

(57) ABSTRACT

The present invention generally relates to a process for the preparation of aqueous solutions of hyperpolarized molecules ready for use in in-vivo MR diagnostic imaging, the use thereof as MRI contrast agent in investigation methods for producing diagnostic MR images of a human or non-human animal body organ, region or tissue.

14 Claims, No Drawings

(56) References Cited

OTHER PUBLICATIONS

Wang, Chao et al., Broader, greener, and more efficient: recent advances in asymmetric transfer hydrogenation, Chemistry, An Asian Journal Oct. 6, 2008, vol. 3, No. 10, Aug. 27, 2008, pp. 1750-1770, XP002538145.

Wilson, David M. et. al., Generation of hyperpolarized substrates by secondary labeling with [1,1-C-13] acetic anhydride, Proceedings of the National Academy of Sciences of the United States of America, vol. 106, No. 14, Apr. 2009, pp. 5503-5507, XP002641409.

Aime, Silvio et al., "Synthesis and NMRD Studies of Gd3+ Complexes of Macrocyclic Polyamino Polycarboxylic Ligands Bearing beta-Benzyloxy-alpha-propionic Residues", Inorganic Chemistry, American Chemical Society, Easton, US, vol. 31, No. 6, Mar. 18, 1992, pp. 1100-1103, XP002120082, ISSN: 0020-1669, DOI: 10.1021/IC00032A035.

European Search Report for application No. EP11191872.8, mail date Apr. 12, 2012.

European Search Report for European application No. EP11184825.5, mail date Feb. 10, 2012.

Gallagher, Ferdia A. et al., "Detection of tumor glutamate metabolism in vivo using 13C magnetic resonance Spectroscopy and hypepolarized [1-13C]glutamate", Magnetic Resonance in Medicine, vol. 66, No. 1, Feb. 17, 2011, pp. 18-23, XP055045198, ISSN: 0740-3194, DOI: 10.1002/mrm.22851.

Gallagher, Ferdia A. et al., "Production of hyperpolarized [1,4-13C2]malate from [1,4-13C2]furmarate is a marker of cell necrosis and treatment response in tumors", Proceedings of the National Academy of Sciences, Jan. 1, 2009, XP055045201, ISSN: 0027-8424, DOI: 10.1073/pnas.0911447106, pp. 19801-19806.

Hovland, Ragnar et al., "Preparation and In Vitro Evaluation of Godota-(BOM)4; A Novel Angiographic MRI Contrast Agent", Org. Biomol Chem., vol. 1, Apr. 10, 2003, pp. 1707-1710, XP002672385.

PCT International Preliminary Report on Patentability for PCT/EP2012/070187, mail date Apr. 15, 2014.

PCT International Preliminary Report on Patentability for PCT/EP2012/074292, mail date Jun. 19, 2014.

PCT international Search Report and Written Opinion for PCT/EP2012/070187, mail date Dec. 4, 2012.

PCT International Search Report and Written Opinion for PCT/EP2012/074292, mail date Jan. 30, 2013.

Viale, Alessandra et al., "Current concepts on hyperpolarized molecules in MRI", Current Opinion in Chemica Biology, Current Biology Ltd., London, GB, vol. 14, No. 1, Feb. 1, 2010, pp. 90-96, XP026895607, ISSN: 1367-5931, DOI: 10.1016/J.CBPA.2009.10.021.

\* cited by examiner

PROCESS FOR PREPARING HYPERPOLARIZED SUBSTRATES AND METHOD FOR MRI

CROSS-REFERENCE TO RELATED APPLICATIONS

This application is the national stage application of corresponding international application number PCT/EP2011/055485 filed Apr. 8, 2011, which claims priority to and the benefit of European application no. EP10159303.6, filed Apr. 8, 2010, all of which are hereby incorporated by reference in their entirety.

The present invention generally relates to the field of Magnetic Resonance Imaging (MRI). More particularly, the invention relates to a process for the preparation of aqueous solutions of hyperpolarized molecules ready for use in in vivo MR diagnostic imaging, the use thereof as MRI contrast agent in investigation methods for producing diagnostic MR images of a human or non-human animal body organ, region or tissue.

BACKGROUND OF THE INVENTION

MRI is a non invasive technique with broad diagnostic value. The technique has gained wide clinical acceptance and is of great importance in diagnostic medicine. However, despite significant technological advancements (increasing field strength and cooling of electronics), applications of MRI are limited by an intrinsically low sensitivity.

Some alternatives to enhance its sensitivity have been developed which involve ex vivo nuclear spin polarization of agents, prior to administration and consequent in vivo MR signal measurement.

EP 1544634 discloses some of said alternative techniques, comprising among others, Dynamic Nuclear Polarisation (DNP), Para Hydrogen Induced (PHI) polarisation and Polarisation Transfer from a hyperpolarised noble gas.

In particular, U.S. Pat. No. 6,466,814 describes a method of magnetic resonance investigation comprising the production of a hyperpolarised solution of a proper high T1 agent selected from a series of possible candidates, followed by the administration of said solution to a subject.

During hyperpolarisation of a sample (particularly as regards the DNP methods), very low temperature are often required in order to have the sample polarised in a proper solid form. In this respect, it is known in the art (see e.g. US2008095713) that successful polarization levels are generally achieved by DNP technique when the mixture upon freezing forms a glass rather than a crystallized sample.

The applicant noticed that while many molecules (e.g. carboxylic acids) are not capable of forming a glass in their pure form as such, thus requiring the addition of a glass-forming agent thereto, some precursors thereof (e.g. anhydrides or esters) are instead capable of forming a neat glass substantially without the need of any glass-forming additive.

Furthermore, other substrates may have stability problems, so that they are easily and quickly degraded into non active substances or non desired compounds. For instance, some active substrates can be transformed, at least in part, into their respective non-active isomers.

Hence, according to the invention, the use of a stable DNP hyperpolarised precursor which can readily be transformed into the desired hyperpolarized substrate upon dissolution in an aqueous carrier (e.g. an anhydride or an ester precursor of a carboxylic acid), is particularly advantageous. Applicant has further observed that certain final substrates may be obtained with a higher degree of polarization if the DNP polarisation is effected on their respective precursors (e.g. an ester) rather than on the molecule of the substrate itself (e.g. the respective carboxylic acid).

Hence, according to the invention, the use of a stable precursor which can readily be transformed into the desired hyperpolarized substrate upon dissolution in an aqueous carrier, such as an anhydride or an ester precursor of a carboxylic acid, is particularly conveniently.

Advantageously, suitably selected precursors may be used to prepare two or more different hyperpolarized substrates there from, or a mixture of a hyperpolarized substrate with a hyperpolarized MR contrast agent or a hyperpolarized pH reporter.

For these and other advantages which may be better appreciated by the skilled person upon reading the detailed description of the invention, the present invention provides a substantial innovative contribution over the state of the art.

SUMMARY OF THE INVENTION

A first aspect of the invention relates to a process for preparing a hyperpolarized active substrate for use in a method of magnetic resonance investigation, which comprises the steps of:

a) preparing a hyperpolarized precursor of said substrate by dynamic nuclear polarisation (DNP) methods; and b) contacting said hyperpolarized precursor with an aqueous carrier to transform it into said hyperpolarized active substrate.

In a preferred embodiment of the invention, the precursor is a compound which, upon contact with water is transformed, preferably by hydrolysis thereof, into the corresponding polarized active compound, preferably one or more carboxylic acid, either in undissociated (i.e. neutral) or dissociated (i.e. anionic) form. According to a further preferred embodiment, said precursor is selected from the group consisting of anhydrides, diketenes, esters, lactones and amides.

Even more preferred are those esters precursors that upon hydrolysis give the corresponding hyperpolarised acid having a degree of polarisation higher than the degree of polarisation otherwise obtainable by directly hyperpolarising the acid itself. To this extent, preferred esters are liquids below 130° C., preferably below 100° C., most preferably below 35° C. and forms glasses (non-crystalline solids) when rapidly frozen, e.g. when inserted into liquid nitrogen or liquid helium. The precursors of the invention can be hydrolysed in an acidic (i.e. pH<7), basic (i.e. pH>7) or neutral (i.e. pH=7) aqueous carrier.

Typically carriers are selected from aqueous carrier such as: ionised water, saline solution, optionally comprising an additive such as a buffer, an enzyme and the like.

In another preferred embodiment, the transformation of the precursor into the active substrate according to the present invention is effected by hydrolysis in the presence of an enzyme.

Examples of suitable enzymes are hydrolases (generally indicated with EC 3 or even EC 3.x.x.x) particularly preferred being esterases, acylases, lipases.

In another aspect, the present invention relates to a method for operating an MRI system comprising the steps of:

a) submitting a subject, which has been positioned in said MRI system and treated with a hyperpolarized active substrate obtained from a precursor according to the above process, to a radiation frequency selected to excite nuclear spin transitions in a non-zero nuclear spin nuclei of said active substrate; and b) recording a MR signal from said excited nuclei.

In a further aspect, the present invention relates to a method for operating a MRI system comprising the steps of:

a) submitting a subject pre-treated with a hyperpolarized active substrate obtained from a precursor according to the above process, which has been positioned in said MRI system, to a radiation frequency selected to excite nuclear spin transitions in a non-zero nuclear spin nuclei of said active substrate; and b) recording a MR signal from said excited nuclei.

DETAILED DESCRIPTION OF THE INVENTION

The present invention provides an alternative method for the ex vivo hyperpolarization of molecules of biological interest, particularly those molecules (metabolites) which are part of metabolic pathways such as, for instance, tricarboxylic acid (TCA) cycle (also known as citric acid cycle), glycolysis, beta-oxidation, urea cycle and ketobody metabolic pathways.

Therefore, the invention relates to a process for the preparation of a hyperpolarized active substrate, said process comprising the steps of:

a) preparing a hyperpolarized precursor of said active substrate by Dynamic Nuclear Polarisation (DNP) methods; and b) contacting said hyperpolarized precursor with an aqueous carrier to transform it into an active hyperpolarized substrate.

The expression "hyperpolarized precursor" comprises within its meaning any hyperpolarized molecule which, upon contact with an aqueous carrier, is transformed into at least one active substrate.

The expression "aqueous carrier" comprises within its meaning any aqueous solvent, solvent mixture or solution that is tolerated by the human or non-human animal body, for use in in-vivo diagnostic applications.

Generally, the carrier is sterile and physiologically tolerable, such as sterile water, purified water such as water for injection (WFI), physiological saline solution, optionally properly buffered. The carrier may optionally comprise a suitable amount of a selected additive (e.g. a base or an acid), capable of promoting the rapid and selective conversion of the hyperpolarized precursor into a water soluble active substrate.

In this respect, the additives, when present, are physiologically acceptable ones, and are employed in relatively low amounts, e.g. comprised from 0.1 mole equivalents to 10 mole equivalents, preferably from 1 mole equivalent to 4 mole equivalent (where mole equivalents means amount of additive relative to the amount of hyperpolarized precursor), in order to provide physiologically acceptable solutions ready for injection. In some cases, e.g. when the amount of additive added to promote the transformation of the precursor is relatively high, the obtained aqueous solution (comprising the hyperpolarized active substrate) may subsequently be admixed with further additives in order to render it physiologically acceptable for in vivo diagnostic applications. For instance, the pH of the solution may subsequently be adjusted at physiologically acceptable values by adding suitable acid or basic buffers thereto, before administration thereof. In this respect, examples of suitable additives are pH regulating agents such as organic or inorganic bases (e.g. alkaline metal bases) or organic or inorganic acids or buffers.

According to a preferred embodiment, the transformation of the precursor into the active substrate is effected by hydrolysis.

As used herein the term "hydrolysis" comprises a chemical reaction in which water reacts with a starting compound to produce one or more resulting compound(s); it typically involves the splitting of a bond on the starting compound and the addition of a hydrogen cation and/or of a hydroxide anion to the structure of the starting compound, to obtain the resulting compound(s).

Said hydrolysis reaction can be carried out under acidic (pH<7), basic (pH>7) or even neutral conditions (pH=7), whereas basic conditions are preferred, as will be described herein below in more details. In this direction, and as previously mentioned, the selected aqueous carrier can contain as additive either a suitable amount of alkaline base such as hydroxides or carbonate, like NaOH or $NaHCO_3$, or $Na_2CO_3$, as well as other organic or inorganic compounds with basic aqueous reaction (e.g. trimethylol aminomethane, also known as trimethylol aminomethane, also known as tromethamine, or trisodium phosphate); or an inorganic or organic acid capable of promoting the hydrolysis of a hyperpolarized precursor such as, among others, phosphoric acid, hydrochloric acid, citric acid or acetic acid.

Particularly preferred additives for the method of the instant invention are sodium hydroxide (NaOH), and hydrochloric acid (HCl).

According to a particular preferred embodiment, an aqueous solution of the hyperpolarized precursor in a 10-100 mM concentration is hydrolyzed in the presence of 10-400 mM NaOH. The hydrolysis of the hyperpolarised precursor practically occurs by adding the same to a carrier selected as formerly described, at a temperature from about 20° C. to 100° C., preferably from 40° C. to 70° C., to obtain an aqueous solution containing the desired hyperpolarised active product or mixture of products, basically depending on the chemical nature of the precursor.

To this extent, the precursor shall be capable of being quantitatively transformed into the desired hyperpolarized active substrate upon contact with the aqueous carrier, as formerly described. The expression "hyperpolarized active substrate" (also referred to as "substrate" in the following of this specification) comprises within its meaning high T1 compounds containing non-zero nuclear spin nuclei capable of exhibiting a long T1 relaxation time. Long T1 relaxation times are to be intended as time values sufficiently long to allow an effective detection of the signal.

In the present application, the expression "quantitative transformation" is intended to indicate a transformation (preferably a hydrolysis) in the amount of 20% or more, preferably 50% or more, more preferably 75% or more and even more preferably of at least 90%, particularly preferred being a transformation of at least 95% of the precursor into the active substrate.

For each preferred embodiment of the present invention, the precursors comprise those compounds which upon hydrolysis reaction provide a corresponding carboxylic acid (in a non-dissociated or dissociated form), alone or in admixture with one or more side reaction product, the latter preferably being pharmaceutical acceptable.

Preferably, the precursor compound is enriched with non-zero nuclear spin nuclei, such as 13C, 19F and/or 15N nuclei, preferably 13C. The term "enriched" means that the concentration of the non-zero spin nuclei in the compound is above the typical value of natural abundance of said nuclei, preferably above at least 10% of natural abundance, more preferably above at least 25%, and even more preferably above at least 75% of its natural abundance and most preferably above at least 90% of its natural abundance. The enrichment will in particular be concentrated on an atom position, for which a chemical transformation of the molecule, or a chemical or magnetic changes of the environment of the molecule, will be measurable as a change of its chemical shift. Said non-zero nuclei confer to the substrate a T1 relaxation time of at least 5 seconds (indicated with s), preferably of at least 10 s, preferably of at least 20 s, preferably of at least 30 s, and even more preferably of at least 40 s, measured in a solution subjected to a magnetic fields of from about 0.5 mT to about 20 T (Tesla). The enrichment may include either selective enrichments of one or more sites within the molecule or uniform enrichment of all sites. To this extent, commercially available enriched precursors can be suitably employed or, in case, the enrichment of choice can be achieved by chemical synthesis, or biological labeling, according to well known prior art teachings.

Being obtained from the respective precursors, the active substrates will correspondingly be enriched with respective non-zero nuclear spin nuclei, such as 13C, 19F and/or 15N nuclei, preferably 13C.

It has to be noted that the signal of any hyperpolarized imaging agent decays due to spin relaxation. Hence, the final hyperpolarized active substrate, particularly when in solution, shall maintain its polarization for a sufficiently long period of time, in order to allow the imaging procedure to be carried out within a relatively comfortable frame of time. Preferably, the T1 value of the hyperpolarized precursor and of the hydrolyzed substrate shall thus be of at least 5 seconds or higher, preferably of 10 s seconds or higher, more preferably at least 30 s seconds and even more preferably of 50 s seconds or higher. Particularly preferred are those substrates for which the T1 value is of 70 s seconds or higher, and even more particularly preferred are those having a T1 value of 100 s seconds or higher. Said T1 values are referred to values measured typically at a field strength of from 0.5 mT to 20 T and at a temperature of from 25° C. to 70° C., in particular at a field strength of 1.5-3 T and at a temperature of 37° C. When outside the body, said T1 values are generally measured at a field strength of 0.5 mT and at a temperature of 60° C. According to a further embodiment, the above mentioned non-zero spin nuclei can be directly linked to one or more Deuterium atom, typically with the intention to prolong the T1 values of the final hyperpolarized compound (see in this direction, US 2008/0287774 A1, herein included by reference). By that, many more metabolites can advantageously be distinguished from their substrates on the basis of the larger chemical shift dispersion thus available, and, even more advantageously, the Deuteration of hyperpolarized non-zero nuclear spins can expand the group of possible non-zero nuclear spins useful for the imaging of final hyperpolarized compounds and their metabolites. Deuteration is in fact particularly useful for instance in those cases where the chemical shifts of the substrate and the chemical shifts of the metabolites thereof are very similar to each other, or even too close one to each other to be otherwise distinguished or detected. A representative example of what stated above can be the case of the compound glycine, where the substrate glycine contains one long T1 position (1-C) when non-deuterated, and two long T1 positions (1-C and 2-C) when deuterated. Of note, whilst the 1-C position exhibit little chemical shift differences to its expected main metabolites (less than 0.5 ppm) the 2-C position on the contrary show several ppm (up to 9 ppm) chemical shift differences to the equivalent position in the expected metabolites.

Remarkably, the active substrates obtained from the corresponding hyperpolarized precursors, according to the present invention, are in particular capable of exhibiting a change in chemical shift in response of a change of physiological conditions (e.g. changes in the pH, $pO_2$, $pCO_2$, redox potential, temperature or ionic concentrations in the vascular system) or a consequence of metabolic activities, such as cellular uptake, cytosolic reactions such as transaminase reactions (comprising amino acids e.g. aspartate and keto acids e.g. oxaloacetate) and glycolysis (comprising carbohydrates e.g. glucose), mitochondrial reactions such as TCA cycle reactions (comprising molecules which are hydrated e.g cis-acontate), redox reactions (comprising ketobodies e.g. acetoacetate) or betaoxidations (comprising short and medium chain fatty acids e.g. butyrate).

Preferred active substrates will for instance exhibit a chemical shift difference of more than 1.5 ppm for quaternary carbon, 2.1 ppm for deuterate methine, 4.2 ppm for deuterated methylene, and 5.4 ppm for deuterated methyl groups, at a filed of 3 T. While the process of the invention is suitable for preparing any such molecules, it is particularly advantageous for the preparation of hyperpolarized molecules for which the direct ex-vivo hyperpolarization thereof may pose some problems, or it is obtained with a low degree or it is even too difficult to be realised. In fact, while many molecules (e.g. carboxylic acids) are not able of forming a glass in their pure form, so that it is necessary to admix the substrate with a glass-forming additive, their precursors according to the present invention, e.g. anhydrides or esters, preferably ethyl ester, are indeed able of forming said required neat glass, without the need of any further glass-forming additive. In other instances, the active substrate, such as carboxylic acid or carboxylate, may also pose some stability issues such as isomerisation or chemical decomposition. Thus, according to the invention, the use of a precursor which does not pose stability issues, and which can readily be transformed into the desired hyperpolarized substrate upon dissolution in an aqueous carrier (e.g. an anhydride precursor or an ester precursor of a carboxylic acid), is particularly advantageous.

Even further, the process of the present invention is also very convenient where hyperpolarised precursors, such as an ester precursor of a carboxylic acid, are characterised in having advantageous properties, compared to their corresponding active substrates (e.g. glass forming properties leading to a higher degree of hyperpolarization), thereby their hydrolysis lead to the corresponding active substrate having a higher degree of polarisation (typically increased by a factor of 1.5 to 4), with respect to the degree otherwise obtainable by directly hyperpolarising the active substrate itself. In more detail, according to all the above preferred embodiments, preferred precursors, together with the hydrolysis products thereof, comprise, for instance, the following derivatives, and respective hydrolyzed substrates thereof:

1a)

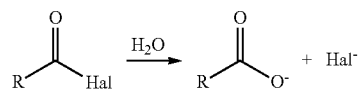

wherein Hal is an halogen atom (F, Cl, Br, I) and R is a C1-C6 alkyl or alkene, cycloalkyl or cycloalkene, arylalkyl or heteroarylalkyl radical, optionally branched and/or substituted with one or more additional functional groups such as —OH, COOH, —NH$_2$, —NHCH$_3$, —N(CH$_3$)$_2$, SH, SCH$_3$; or R is a carbonyl group of formula —CO—Z, wherein Z is: hydrogen, —OH, optionally substituted C1-C6 alkyl, C1-C6 alkoxy, aryl or benzyl group;

1b)

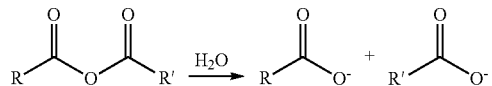

wherein R is as defined in point 1a), and R' is an optionally substituted alkyl, aryl, cycloalkyl, aryl radical (or any of its combination) which by hydrolysis leads to the release of RCOOH and R'COOH, being R'COOH either the same as RCOOH (symmetric anhydrides) or is a different physiologically acceptable carboxylic acid (mixed anhydrides); in this latter case, it can be a different active substrate, a pharmaceutically active compound or simply a non-toxic substance (where "non-toxic substance" as herein defined identifies compounds with an LD50>0.1 mmol/Kg).

1c)

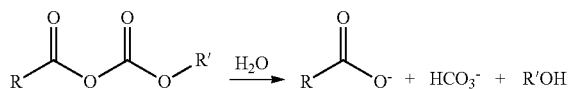

wherein R is as defined in point 1a), and R' is an alkyl, aryl, cycloalkyl, aryl radical (or any of its combination) which by hydrolysis lead to the release of RCOOH and R'OH, where R'OH is an hydroxyl- or hemiacetal-functionalized physiologically acceptable compound (i.e. different active substrate, a pharmaceutically active compound or a non-toxic substance).

1d)

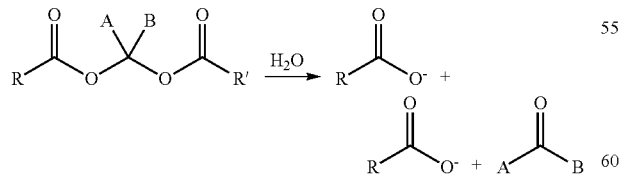

wherein R is as defined in point 1a), and R' is defined as in point 1b) and A and B are such as hydrolysis lead to release of RCOOH, R'COOH (defined as above) and a physiologically acceptable carbonyl compound A-C(=O)—B.

1e) Compounds of General Formula:

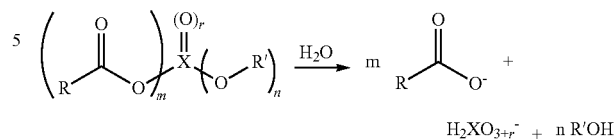

wherein R is as defined in point 1a), and R' is defined as in point 1b) or hydrogen; X=B, P; m+n=3; r=0-1.

1f) Compounds of General Formula:

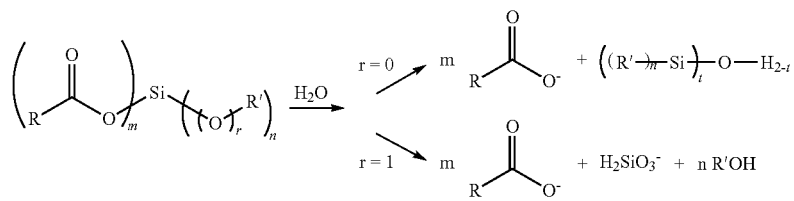

wherein R is as defined in point 1a), and R' is defined as in point 1b) or hydrogen; m+n=4; r=0-1; t=1-2 and the silicon-containing molecule is a physiologically acceptable compound or is easily and rapidly removed by methods known in the art.

1g) Compounds of General Formula:

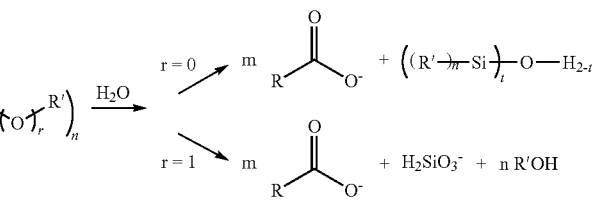

wherein R is as defined in point 1a) and m+n=2, r=1-2, and the sulfur-containing ion is a physiologically acceptable compound or is easily and rapidly removed by methods known in the art.

1h) Compounds of General Formula:

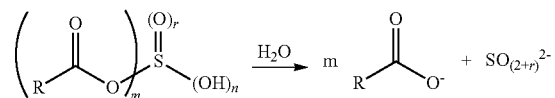

wherein R is as defined in point 1a), and Y is a non-metal chosen among B, N, Si, P, S, substituted with groups such upon release of the carboxylic acid RCOOH leads to non-metal compounds of B, N, Si, P, S.

1i) Compounds of General Formula:

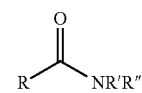

wherein R is as defined in point 1a), and R' and R'' are each independently hydrogen or corresponding to the R group as defined in point 1a) or substituents leading to faster hydrolysis, for instance azoles, such as:

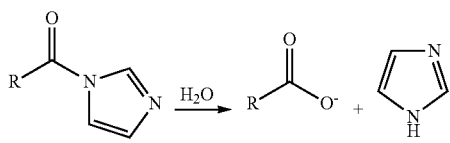

or their ring-substituted and N-quaternized derivatives.

1l) Compounds of General Formula:

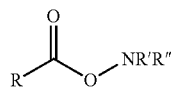

wherein R is as defined in point 1a), and R' and R" are suitable acyl groups such as:

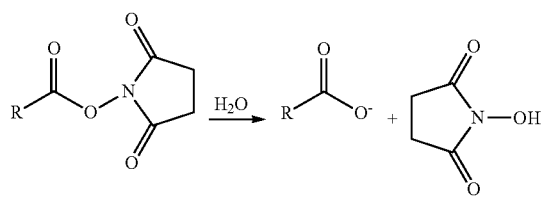

or their ring-substituted and optionally salified derivatives.

1m) Compounds of General Formula:

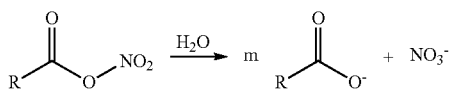

wherein R is as defined in point 1a), and

2) Cyclic Anhydrides of General Formula:

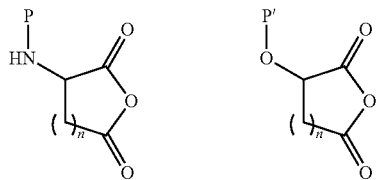

wherein
n=1, 2
P=hydrogen or amino protecting group,
P'=hydrogen or hydroxy protecting group, 2a) Saturated or Unsaturated Cyclic Anhydride of Formula:

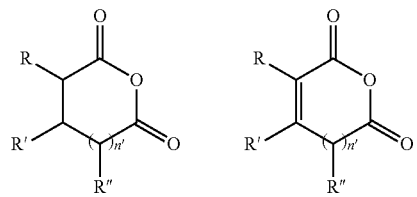

wherein
R is defined as in point 1a),
R', R" are independently defined as R or hydrogen,
n'=0, 1 which according to the following hydrolysis reaction scheme provide the corresponding carboxylates:

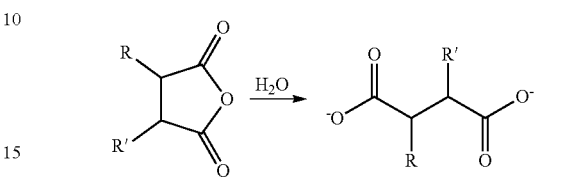

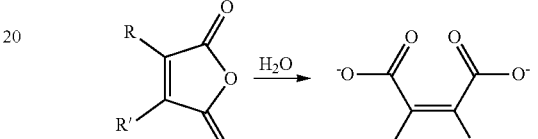

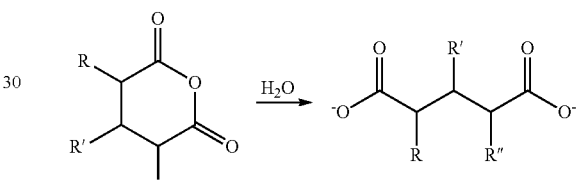

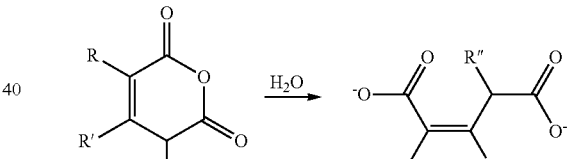

3) Esters and Hydrolyzed Substrates of the General Formula:

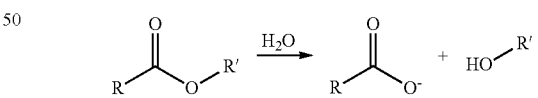

wherein R is defined as in point 1a) and R' as defined under 1b).

4) Ketenes of General Formula:

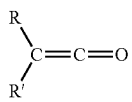

wherein R is defined as in point 1a) and R' is independently defined as R or hydrogen.

4a) Ketene Cyclic Dimers (Diketenes) which Upon Hydrolysis According to the Following Scheme Provide the Desired Carboxylate:

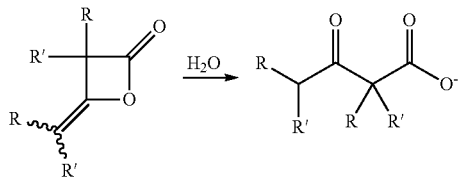

wherein each R and each R' are respectively independently defined as in point 4).

4b) Acyclic Ketene Dimers (Acylketenes) which Upon Hydrolysis According to the Following Scheme Provide the Desired Carboxylate:

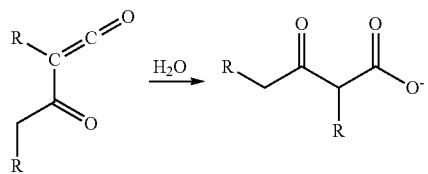

wherein each R is independently defined as in point 1a).

4c) Ketene Adducts with Carbonyl Compounds which Upon Hydrolysis According to the Following Scheme Provide the Desired Carboxylate:

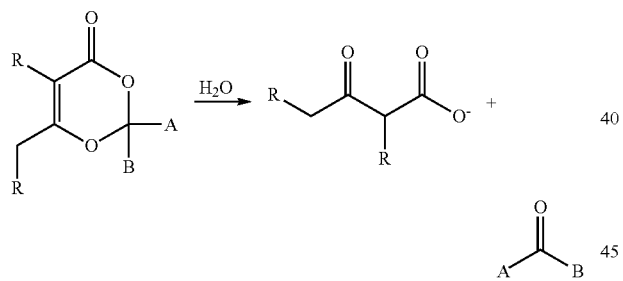

wherein each R is independently defined as in point 1a) and A and B are defined as in point 1) iv).

5) Precursors Specific for Aminoacids Selected According to the Schemes Below:

5a) N-Carboxyanhydrides of General Formula which Upon Hydrolysis According to the Following Scheme Provide the Desire Carboxylate:

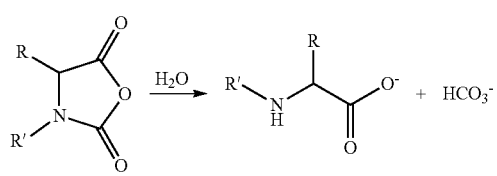

wherein R and R' are chosen as to correspond to naturally occurring aminoacids of formula R'NH—CH(R)—COOH.

5b) Metal Chelates of Aminoacids of General Formula which Upon Hydrolysis According to the Following Scheme Provide the Desire Carboxylate:

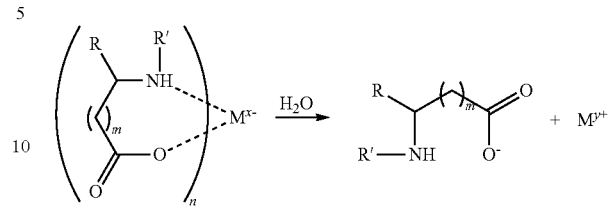

wherein R and R' are chosen as to correspond to naturally occurring aminoacids of formula R'NH—CH(R)—(CH2)m-COOH, with m=0-3, n=1-3 and x– is the overall charge of the complex with –1<x<+1, y+ is the charge of the metal ion and y=1-3, M is a biologically compatible diamagnetic metal ion. Charged complexes are preferably salified with polyhydroxyamines or polyhydroxyacids.

6) Precursors Specific for Hydroxyacids, According to the Schemes Below:

6a) O-Carboxyanhydrides of General Formula:

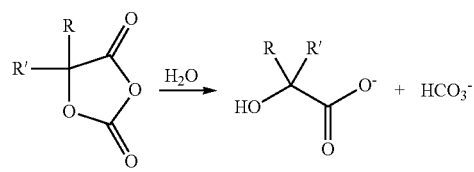

where R and R' are chosen as to correspond to naturally occurring hydroxyacids of formula HO—CRR'—COOH.

6b) Lactones of General Formula:

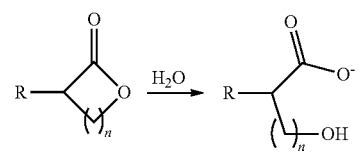

where R is defined as in point 1a) and n=0-3.

6c) Dilactones of General Formula:

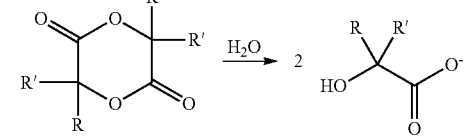

wherein R and R' are each independently chosen as to correspond to naturally occurring hydroxyacids of formula HO—CRR'—COOH.

6d) Metal Chelates of Hydroxyacids of General Formulas:

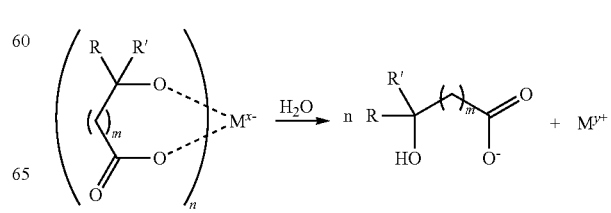

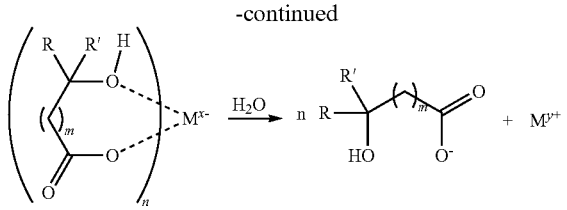

wherein R and R' are defined as in point 5b); m=0-2; n=1-3 and x− is the overall charge of the complex with −2<x<4, y+ is the charge of the metal ion and y=1-3, M is a biologically compatible diamagnetic metal ion. Charged complexes are preferably salified with polyhydroxyamines or polyhydroxyacids.

7) Precursors Specific for Ketoacids, According to the Following Hydrolysis Reaction Scheme:

7a) Enol Form of Keto Acids of General Formula:

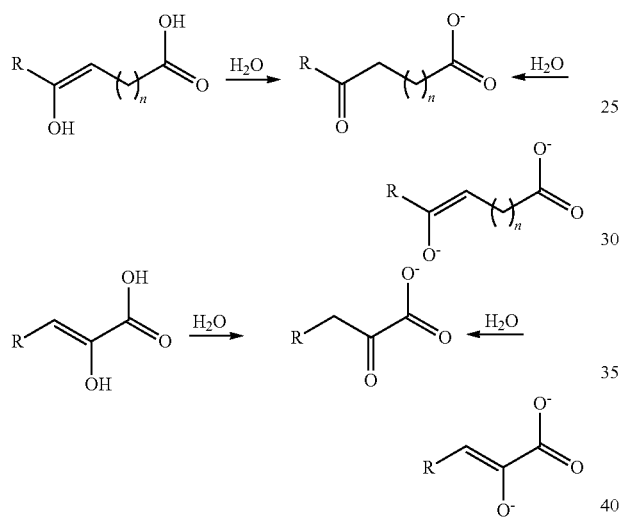

wherein R is defined as in point 1a) and n=0-2, and their corresponding salts ("enolate") with one or more biologically compatible metal ions or preferably salified with polyhydroxyamines or polyhydroxyacids.

7b) Metal Chelates of Ketoacids, the Latter Either in their Deprotonated Ketoacid Form or in their Deprotonated Enol Form, of General Formula:

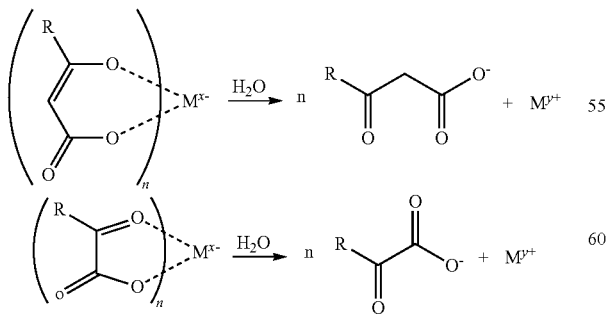

wherein R is defined as in point 1a) and M is a metal ion, n=1-3 and x− is the overall charge of the complex with −2<x<4, y+ is the charge of the metal ion and y=1-3, M is a biologically compatible diamagnetic metal ion. Charged complexes are preferably salified with polyhydroxyamines or polyhydroxyacids.

Particularly preferred examples of said precursors include, but are not limited to, organic cyclic or linear anhydrides either symmetric or mixed, such as butyric anhydride, butyric-acetic anhydride, succinic anhydride or cis-aconitic anhydride; cyclic or acyclic diketenes, such as 4-methylideneoxetan-2-one; ester derivatives either cyclic (i.e. lactones) or linear, such as acetoacetate derivatives, e.g. ethyl acetoacetate, ethylsuccinate (mono or di-ester), ethyl-pyroglutamate, dimethylglycine ethyl ester, ethyl 2-oxothiazolidine-4-carboxylate, 2-oxoglutarate ethyl ester (mono or di-ester), ethylmalate (mono or di-ester); amides such as N-acetyl aminoacids (e.g. N-acetylglutamine or N-acetylglycine).

In a still preferred embodiment, the precursor is selected from:

Butyric anhydride:

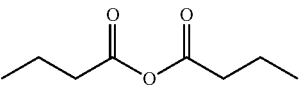

butyric-acetic anhydride:

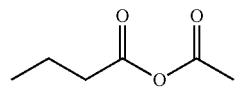

cis-Aconitic anhydride:

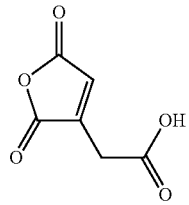 [SMILES: O=C(O)CC1=CC(=O)OC1=O]

4-Methylideneoxetan-2-one:

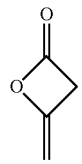

Ethylacetotacetate:

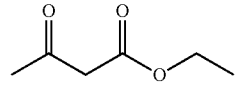

Succinic ethyl ester (mono or di-ester):

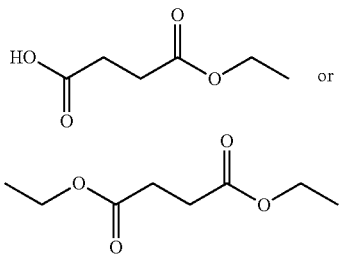

Ethylpyroglutamate:

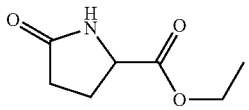

Dimethylglycine ethyl ester:

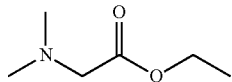

2-Oxothiazolidine-4-carboxylic ethyl ester:

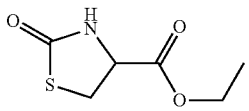

2-Oxoglutaric ethyl ester (mono or di-ester):

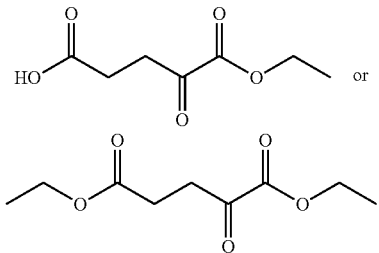

Malic ethyl ester (mono or di-ester):

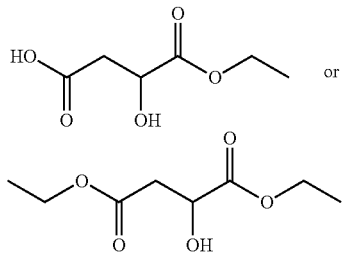

Phenylalanine ethyl ester:

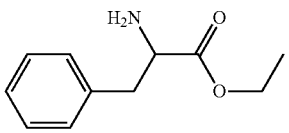

N-Acetylglutamine or N-Acetyl glycine:

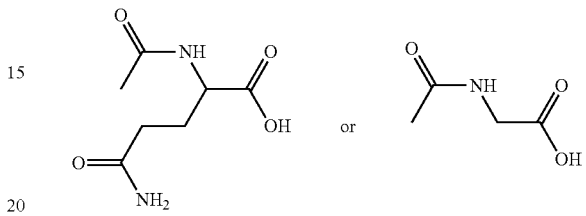

Even more preferably, said precursors are 13C labeled and optionally deuterated, whereas preferred ones are selected from: 1,1'-13C-2-butyric anhydride, 1-13C-butyric-acetic anhydride, 6-13C-cis-aconitic anhydride, 4-methylideneoxetan-2-13C-one, 1-13C-ethyl acetotacetate, 1, 3-13C-2-ethyl acetotacetate, 1, 4-13C-2-succinate-(1)-ethyl ester, 1-13C-ethylpyroglutamate, 2-13C-d2-dimethylglycine ethyl ester, 1-13C-ethyl 2-oxothiazolidine-4-carboxylate, 1-13C-2-oxoglutarate-(1)-ethyl ester, 1, 4-13C-2-ethylmalate, 5-13C—N-acetylglutamine or 2-13C-2d-N-acetyl glycine.

In more detail, preferred substrates include, carboxylic acids, including mono-, di- and tri-carboxylic acids both in their dissociated (preferably) or undissociated form, optionally containing one or more of the following moieties: hydroxyl (hydroxy acids), carboxy (ketoacids) or amino (amino acids).

Examples of suitable carboxylic acids substrates (preferably in their carboxylate form) include:

R—COOH, where R represents $C_1$-$C_{10}$ alkyl, $C_1$-$C_{10}$ oxo-alkyl, $C_1$-$C_{10}$ hydroxy-alkyl, $C_1$-$C_{10}$ amino-alkyl, $C_1$-$C_{10}$ alkene, R—(COOH)$_2$, where R represents $C_1$-$C_{10}$ alkyl, $C_1$-$C_{10}$ oxo-alkyl, $C_1$-$C_{10}$ hydroxy-alkyl, $C_1$-$C_{10}$ amino-alkyl, $C_1$-$C_{10}$ alkene, and where the carboxylic groups are bound to two different carbon atoms of R;

R—(COOH)$_3$, where R represents $C_1$-$C_{10}$ alkyl, $C_1$-$C_{10}$ oxo-alkyl, $C_1$-$C_{10}$ hydroxy-alkyl, $C_1$-$C_{10}$ amino-alkyl, $C_1$-$C_{10}$ alkene, and where the carboxylic groups are bound to three different carbon atoms of R.

Specific examples of high T1 hyperpolarized carboxylic acid substrates (in their carboxylate form) include, for instance, butyrate, acetoacetate, cis-aconitate, 2-oxobutyrate, 2-hydroxybutyrate, (R)-3-hydroxybutyrate, crotonate, succinate, oxaloacetate, malate, fumarate, citrate, isocitrate. Examples of suitable substrate are disclosed for instance in U.S. Pat. No. 6,278,893, here incorporated by reference.

Thus, preferred hyperpolarized substrate/precursor systems are selected from: acetoacetate/acetoacetate ethyl ester, butyrate/butyric anhydride, glycine/N-acetyl glycine, succinate/succinic-(1)-ethyl ester, phenylalanine/phenylalanine ethyl ester, glutamine/N-acetyl glutamine, 2-oxoglutarate/2-oxoglutaric-(1)-ethyl ester, malate/malic-(1)-ethyl ester, pyroglutamate/pyroglutamate ethyl ester, 2-oxothiazolidine-4-carboxylate/2-oxothiazolidine-4-carboxylate ethyl ester and dimethylglycine/dimethylglycine ethyl ester.

Even more preferably, the above acetoacetate, glycine, glutamine and dimethyl glycine substrates are obtained from the indicated precursors by enzymatic hydrolysis, as described herein below, according to a further embodiment of the invention.

Preferred embodiments for the preparation of a hyperpolarized precursor and subsequent transformation into the hyperpolarized active substrate are illustrated hereinafter, wherein the preferred enriched 13C positions are labelled with *, # or a similar mark.

In a preferred embodiment of the invention, a precursor of butyric acid is prepared. Butyric acid is a metabolite in the fatty acid metabolic pathways. One of the primary products of butyric acid metabolism is butanoyl-CoA formed in a reaction, which is catalyzed by acyl-CoA synthetase (EC 6.2.1.2). Butanoyl-CoA can either be converted to crotonoyl-CoA and enter the beta-oxidation pathway ending up in two molecules of acetyl-CoA, or it can be converted to its carnitine ester butanoyl carnitine, according to the following scheme.

one molar equivalent of a base such as NaOH) the hydrolysis of the anhydride DNP-sample proceeds rapidly. While the concentration of the anhydride in the hyperpolarized sample is more or less the same as the concentration of the acid in the glass-forming mixture, the subsequent hydrolysis of an anhydride's molecule provides twice the amount of butyric acid molecules, thus allowing to obtain an almost double concentration of butyric acid. Similarly, also mixed butyric-acetic anhydride forms a glass upon rapid freezing without addition of any glass-forming agents. Also in this case, hydrolysis of the hyperpolarized precursor proceeds rapidly upon contacting the precursor with an aqueous solution with one molar equivalent of NaOH. In this latter case, it can be appreciated that the hydrolysis of the mixed anhydride provides a similar amount of an additional hyperpolarized substrate, in addition to butyric acid.

According to another preferred embodiment, a precursor of acetoacetate is prepared. Acetoacetate is a metabolite in the ketone body metabolic pathway.

One product of Acetoacetate metabolism is 3-hydroxybutyrate a reaction which is catalyzed by the enzyme D-3-

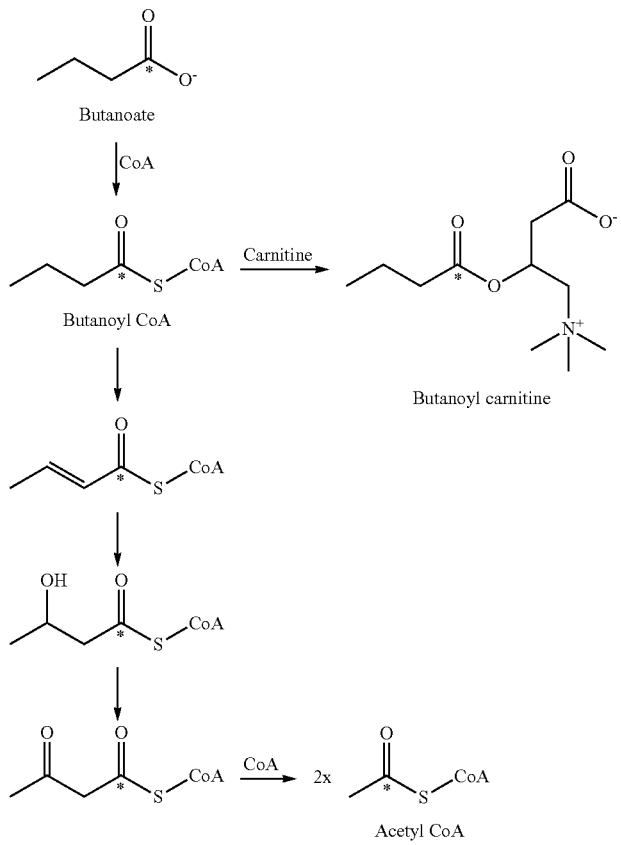

Butyric acid however crystallizes upon rapid freezing, also in the presence of relevant amounts of radical. Hence, it is necessary to add a certain amount of a glass-forming agent (e.g. glycerol or DMSO) to the DNP-preparation of the butyric acid. While this may not be a substantial drawback per se, the fact of admixing butyric acid with a glass forming agent reduces the final concentration of the acid in the DNP-preparation. On the contrary, butyric anhydride forms a glass upon rapid freezing without addition of any glass-forming agents. Furthermore, upon dissolution in an aqueous solution at basic pH (e.g. an aqueous solution with hydroxybutyrate dehydrogenase (HBDH, EC 1.1.1.30). This redox reaction involves the co-enzymes NAD+/NADH. The reaction equilibrium is dependent on the co-enzyme ratio, according to the following scheme:

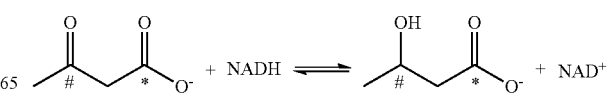

Another reaction of acetoacetate is a reaction catalyzed by the enzyme acetoacetate CoA-transferase (EC 2.8.3.5) to form acetoacetyl-CoA, according to the following scheme:

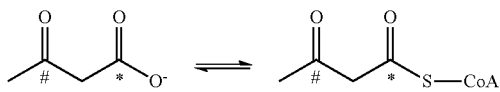

Acetoacetic acid, and its salt acetoacetate, is however difficult to directly hyperpolarize, in view of its inherent instability. In particular, being a β-ketoacid this molecule is prone to decarboxylation even with mild heating. The preparation and dissolution steps in the DNP-process results therefore in decomposition of this compound. Thus, according to the present invention, diketene (4-methylideneoxetan-2-one) is employed as precursor of acetoacetate. Diketene can form a glass upon rapid freezing in the presence of small amounts of glass-forming agent (e.g. 2:1 ratio). Once hyperpolarized, diketene is then promptly converted into acetoacetate upon contact with the aqueous carrier, according to the following hydrolysis reaction scheme:

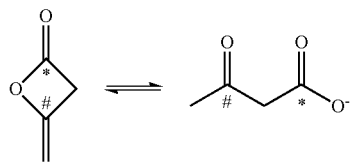

without appreciable degradation of the substrate.

According to another preferred embodiment, a precursor of cis-aconitate is prepared. Cis-aconitate is a metabolite in the TCA cycle.

Cis-aconitate forms citrate and isocitrate in reactions catalyzed by aconitase (EC 4.2.1.3). Even though this enzyme catalyses both the conversion between cis-aconitate and citrate and between cis-aconitate and isocitrate the equilibrium is displaced towards citrate, according to the following reaction scheme:

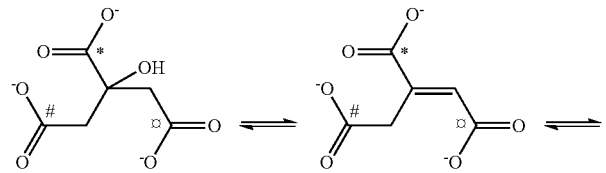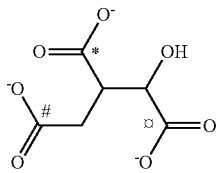

Preparation of cis-aconitate for DNP requires, however, dissolution in substantial amounts of a glass-forming agent, e.g. DMSO, resulting in a rather low final concentration (2-3 M) of the substrate. Furthermore, the thermodynamically stable form is trans-aconitate (an inhibitor of aconitase) and in solution the cis-form is slowly converted to the trans-form, e.g. during the preparation of the DNP-sample. On the contrary, rapid freezing of the cis-aconitate anhydride (from its melting temperature of about 75-80° C.) in $N_2$ produces a glass form. In addition, the required cis-isomer is maintained in the entire DNP-process and in the dissolution of the anhydride in water. In the presence of an aqueous basic solution, the hydrolysis of hyperpolarized cis-aconitic anhydride proceeds rapidly to form the desired hyperpolarized cis-aconitate.

As mentioned above, even more preferred are those esters precursors that upon hydrolysis lead to the corresponding acid showing a degree of polarization higher than the degree of polarization otherwise obtainable by hyperpolarizing the acid itself. In this direction, examples of such esters are those compounds that are liquids below 130° C., preferably below 100° C., most preferably below 35° C. and forms glasses (non-crystalline solids) when rapidly frozen, e.g. when inserted into liquid nitrogen or liquid helium. Once hyperpolarized, typically by DNP method, the above mentioned esters are added to an aqueous carrier, according to the present invention, to achieve the corresponding active substrate derivative, preferably by hydrolysis, having a degree of polarization factor of at least 1.2 times higher than the one obtainable by direct hyperpolarization of the substrate, preferably at least 1.5 and up to e.g. 4 times higher than that obtainable by directly hyperpolarizing the active substrate itself.

To this regard, examples of preferred ester precursor are selected from: itaconate, pyroglutamate, 2-oxothiazolidine-4-carboxylate, and dimethylglycine, as illustrated in the experimental part herein below.

Even more preferably, the above esters precursor are hydrolyzed under basic conditions (i.e. at a pH>7), in the presence of an inorganic alkaline base such as NaOH or an organic base such as trimethylol aminomethane, also known as tromethamine, optionally in the presence of a catalytic enzyme, such as for instance a carboxylesterase.

In this direction, and according to another embodiment of the invention, the transformation of the precursor into an active substrate can also be effected by enzymatic hydrolysis. As used herein the term "enzymatic hydrolysis" comprises an enzymatic reaction in which the speed of the hydrolysis reaction is accelerated and/or the conversion yield of the hydrolysis reaction is increased, for instance with an increase in the conversion yield of at least twice, preferably at least 10 times with respect to the non-enzymatic hydrolysis, resulting in a quantitative (e.g. at least 50%, preferably at least 75% and even more preferably 95%) conversion of the starting compound to produce one or more resulting compound(s). According to this embodiment of the invention, the hyperpolarized precursor, is contacted with an aqueous carrier as previously mentioned, in the presence of an enzyme, at a temperature sufficiently high to melt the hyperpolarized sample and to bring it at a physiological temperature (e.g. about 35-40° C.). During dissolution and heating, the precursor is transformed, typically by enzymatic hydrolysis thereof, into the desired hyperpolarized active substrate(s) and the obtained solution, optionally after removal of the polarizing agent and/or other by-products of the precursor's transformation, is administered to the patient, as required. The selected precursor can be suitably enzymatically hydrolyzed to at least 50%, preferably at least 75%, even more preferably up to more than 95%.

The amount of the enzyme can vary depending on the specific activity of the particular enzyme, whereas typical amounts are from about 50 U to 30 KU, preferably from 60 U to 300 U, even more preferably from 90 to 270 U/mg enzyme; said amounts added to achieve hydrolysis generally within 2 minutes or even faster, e.g. within 10 seconds. Also, the enzymes are physiologically acceptable in the relatively low amounts used in the invention. In some cases, e.g. when the amount of additive added to promote the transformation of the precursor is relatively high, the enzyme in the aqueous solution (comprising the hyperpolarized active substrate) may subsequently be removed, e.g. by any method known in the art (such as ion-exchange or size separation), or the applied enzyme may have been immobilized before being used, and it can therefore be filtered off before the administration of the hydrolyzed hyperpolarized product. Examples of employable enzymes can be selected among those enzymes that perform the hydrolysis of the hyperpolarized precursor within the concentrations (expressed for instance in mM) and on the time-scale of the method (expressed in minutes), and which can be found in the class of enzymes called hydrolases (generally indicated with EC 3, or even with EC 3.x.x.x).

According to a further preferred embodiment, said enzyme is selected from the group consisting of: esterases, acylases and lipases; whereas, the precursor may be suitably selected among those substrates that produce biological acceptable hydrolysis products. In particular, to this extent, preferred substrates are selected from the group consisting of: ethyl esters and N-acylated derivatives of biological active substrates, where particularly preferred are N-acetylated amino acids such as N-acetyl glutamine (which is accordingly enzymatically hydrolyzed to glutamine and acetate), N-acetyl glycine (enzymatically hydrolyzed to glycine and acetate), ethyl esters such as ethyl acetoacetate (which is accordingly enzymatically hydrolyzed to acetoacetate and ethanol), optionally in deuterated form. The enzymatic hydrolysis can be properly carried out by analogy to the hydrolysis reaction as previously described in the present invention in the absence of the enzyme, e.g. under acid (pH below 7), basic (pH higher than 7) or neutral conditions (pH 7), within the same preferred aqueous carriers as described above.

Preferably, the enzymatic hydrolysis is carried out in buffered aqueous solution at the optimum pH and temperature for the enzyme. Therefore, in a particular preferred embodiment, the present invention relates to a process for the preparation of hyperpolarised active substrate, comprising the enzymatic hydrolysis of a DNP hyperpolarised precursor selected from ethyl acetoacetate and N-acetyl glutamine or N-acetyl glycine in trimethylol aminomethane, also known as tromethamine, buffer or phosphate buffer to afford the final metabolic contrast agent of choice, wherein said hydrolysis is carried out in the presence of carboxylesterase (EC 3.1.1.1. at a temperature from 40 to 60° C. and at a pH from 7 to 9) or aminoacylase (EC 3.5.1.14 at a temperature from 40 to 60° C. and at a pH from 7 to 9). According to a practical embodiment, the enzymatic hydrolysis of a selected hyperpolarized precursor is carried out as follow:

a hyperpolarized precursor was hyperpolarized and dissolved in a proper medium, following procedures described in the art. The thus obtained solution containing the hyperpolarized precursor was optimized for the enzymatic hydrolysis (buffer type, pH and temperature), as previously described. Then, the solution containing the hyperpolarized precursor was mixed with an enzyme solution or immobilized enzyme containing the desired enzymatic activity and, after completed hydrolysis, the enzyme was optionally removed from the reaction medium.

It has to be noted that several ways are employable for hyperpolarising the precursor compounds of the present invention. Further details about the possible polarisation methods can be found, for instance, in WO 99/35508 (Nycomed Imaging AS), WO 98/58272 (Nycomed Imaging AS) and WO99/24080 (Nycomed Imaging AS), all herein incorporated by reference.

According to the invention, the hyperpolarized precursor is obtained by Dynamic Nuclear Polarisation (DNP) methods, preferably in the presence of a polarizing agent, as described, for instance, in WO-A-99/35508. Due in particular to their efficient polarization properties, the use of trityl radicals as polarizing agents is preferred, such as, for instance those described in WO-A-99/35508, WO-A-88/10419, WO-A-90/00904, WO-A-91/12024, WO-A-93/02711 or WO-A-96/39367 and herein included by reference.

Briefly, the process comprises in general terms the steps of:

(a) contacting the high T1 precursor with a polarizing agent (DNP preparation), in the presence of a uniform magnetic field at low temperatures;

(b) exposing said polarizing agent to a microwave irradiation of a frequency, properly selected to excite electron spin transitions in said polarizing agent;

(c) dissolving said DNP preparation in an aqueous carrier (hyperpolarized solution); and optionally (d) removing the polarizing agent from the hyperpolarized solution.

An efficient DNP process is best obtained at high magnetic field (3-8 T) and low temperatures (0.5-4° K), typically obtaining a level of polarization of at least 1%, preferably of at least 5% and even more preferably of at least 10%, where polarization is defined by the following equation:

$$P = \frac{N\alpha - N\beta}{N\alpha + N\beta}$$

wherein;

N$\alpha$ is the number of spins in nuclear spin state $\alpha$; and

N$\beta$ is the number of spins in nuclear spin state $\beta$.

The polarizing agent needs to be stable and soluble in the preparation of the high T1 precursor and in an optional admixed glass former in order to obtain a homogenous distribution and an optimal concentration of the electron spin relative to the nuclear spin. Typically, the polarizing agent is added in an amount of from 5 mM to 50 mM to the mixture undergoing DNP, more preferably from 8 to 18 mM.

According to a still preferred embodiment, a radical of the following general formula (I) can advantageously be employed:

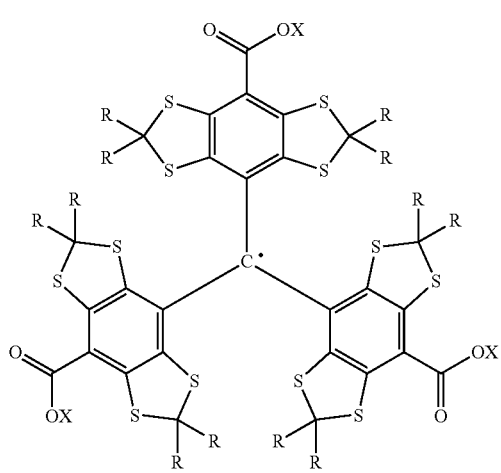

Formula (I)

wherein:

R the same or different, represents a straight chain or branched C1-C6-alkyl group optionally substituted by one or more hydroxyl group, methoxy group, or a group of formula —$(CH_2)_n$—O—R2, wherein n is 1, 2 or 3;

R2 is a straight chain or branched C1-C6-alkyl group, optionally substituted by one or more hydroxyl groups or methoxy groups; and X is independently selected from:
H
an alkaline metal, e.g. Na, K, Cs,
an optionally substituted straight or branched C1-C6 alkyl group, optionally interrupted by Sulphur or Oxygen atoms, an optionally substituted aliphatic or aromatic C3-C8 cyclic group or hetero group.

Preferably, said radical is a compound of the above formula (I) which is soluble in organic liquid precursors to make at least 5 mM solutions e.g. a compound of formula (I), wherein X is hydrogen, or wherein X is selected from hydrophobic moieties such as methyl, ethyl, ter-butyl or phenyl. Also preferred are said radicals, which are insoluble in water, e.g. a compound of formula (I), wherein both X and R are hydrophobic moieties. In case of aqueous DNP preparations of precursors, the preferred radical is (tris(8-carboxy-2,2,6,6-(tetra(hydroxyethyl)-benzo-[1,2-4,5]-bis-(1,3)-dithiole-4-yl)-methyl sodium salt or tris(8-carboxyl-2,2,6,6-tetramethyl-benzo(1,2-d:4,5-dS)bis(1,3)dithiole-4-yl) methyl sodium salt. Optionally, paramagnetic metal ions may be added to the DNP preparation to increase polarisation levels in the compound to be polarised. Examples of suitable paramagnetic metal ions are disclosed for instance in WO-2007/064226 here incorporated by reference. Preferably the paramagnetic metal ion is a paramagnetic chelate comprising $Gd^{3+}$ ions in concentrations from 0.3-4 mM with respect to the metal ion concentration.

Subsequent to the DNP process, the thus hyperpolarized solid sample is transferred into the liquid state. This is typically done by dissolving the sample in an appropriate solvent, or solvent mixture, using suitable devices, as described for instance in WO-02/37132. For the in vivo use, the removal of the trityl radical and of the optional paramagnetic metal ion from the hyperpolarized liquid sample is preferred. To this regard, methods useful to remove the trityl radical and the paramagnetic metal ion are known in the art and described, for instance, in WO-2007/064226. According to the present invention, hyperpolarized compounds obtained from respective precursors as illustrated above, may be monitored using MR spectroscopy or MRI techniques. The analysis can be performed according to common procedures, such as continuous monitoring or single discrete measurements of a series of discrete measurements carried out at suitable intervals of time.

Therefore, in another aspect, the present invention relates to a method of magnetic resonance imaging of a sample, preferably a human or non-human animal body, said method comprising the steps of:

a) preparing a hyperpolarized active substrate with a process which comprises:
i) preparing a hyperpolarized precursor of said substrate; and
ii) contacting said hyperpolarized precursor with an aqueous carrier to transform it into said hyperpolarized active substrate.

b) administering said hyperpolarized active substrate into said sample, c) exposing said sample to a radiation at a frequency selected to excite nuclear spin transitions in said hyperpolarised active substrate, d) detecting MR signals from said active substance, e) optionally generating an image, physiological data or metabolic data from said detected signals.

When the hyperpolarization of the precursor is effected in the presence of a polarizing agent, said polarizing agent is preferably totally or partially separated from the active substrate before administration thereof.

According to the present method, suitable precursors are selected from those hyperpolarized substances which, upon contact with an aqueous carrier are transformed into at least one active substrate, preferably by hydrolysis, as formerly indicated. To this extent, said precursors can be, among others, anhydrides, mixed anhydrides, esters, diketenes and the like. The active substrate is generally present in solution, and the pH of the solution may be adjusted at physiologically acceptable values by adding suitable acid or basic buffers thereto, before administration thereof. The precise concentration will of course depend upon a range of factors such as, inter alia, toxicity and administration route. In general, optimal concentrations will in most cases lie in the range from 10 mM to 150 mM, particularly from 40 to 80 mM. In any case, the dosage of the solution should be kept as low as possible whilst still providing a detectable contrast response. The dosage of the MR imaging substrate employed according to the present method will vary depending on, for instance, the nature of the MR imaging agents used, the tissue or organ of interest and the measuring apparatus.

The hyperpolarized hydrolysed substrate can be administered into the vascular system or directly into an organ or muscle tissue, or by subdermal or subcutaneous route, as the case may be. Then, according to the present method, the sample is exposed to a uniform magnetic field (also known as "primary magnetic field") with radiation of a frequency selected to excite nuclear spin transitions in said hyperpolarised active substrate. The hyperpolarization of the precursor and, consequently, of the active substrate thereof, results in an increasing in the population difference between the excited and ground nuclear spin states of those nuclei which are responsible for the magnetic resonance signals. Since MR signal intensity is proportional to this population difference, the final detected MR signals result in larger amplitude signals. The amplitude of the induced MR signals is also dependent upon several other factors, such as the strength of the magnetic field, the temperature of the sample, the isotopic nature and chemical environment of the imaging nuclei and the like.

In this direction, the chosen procedures for detecting MR signals are those commonly known in conventional MR scanning, such as, multinuclei scanner detection, fast single shot imaging sequences, EPI, RARE and the like. Similarly, the MR signals obtained in the method of the present invention may be conveniently converted into 2- or 3-dimensional image data, into functional, flow or perfusion data, as well as into physiological or metabolic data (e.g. pH, pCO2, temperature or ionic concentrations), by means of conventional manipulations. In particular, the metabolic conversion of the substrate may allow to study metabolic processes in the patient's body and/or provide information on metabolic state of a (healthy or pathological) tissue. It will be clear that the present method should be carried out within the frame of time in which the hyperpolarised active substrate remains significantly polarised, shortly after being subjected to the chemical conversion (e.g. hydrolysis) of the precursor. Therefore, the administration of such active substrate and the subsequent MR measurement are preferably effected as rapid as feasible. This means that the sample, either human or non-human animal body, should be available close to the area in which the polarisation takes place. It has to be noted in this respect that the physical features of the solution to be administered (such as the temperature, density and the like) have to be physiologically tolerable in order to reduce the risks associated with the selected route of administration.

Due to the versatility of the precursors, particularly as regards the mixed anhydrides, the method of the present invention may find clinical application in a variety of imaging investigations such as, but not limited to, the vascular/angiographic imaging, interventional applications, perfusion mapping or metabolic/molecular imaging.

The following examples are intended to better define the invention, without posing any limitation thereof.

EXAMPLES

Materials

The following materials are employed in the subsequent examples:

| | |
|---|---|
| Radical 1 | (tris(8-carboxy-2,2,6,6-(tetra(hydroxyethyl)-benzo-[1,2-4,5']-bis-(1,3)-dithiole-4-yl)-methyl sodium salt |
| Radical 2 | (tris{8-carboxyl-2,2,6,6-tetramethyl-benzo(1,2-d: 4,5-dS)bis(1,3)dithiole-4-yl}methyl) acid form |
| Radical 3 | (tris(8-carboxy-2,2,6,6-(tetra(methoxyethyl))-benzo-[1,2-4,5']-bis-(1,3)-dithiole-4-yl)-methyl) acid form |
| Gadoteridol | 2-[4-(2-hydroxypropyl)-7,10-bis(2-oxido-2-oxoethyl)-1,4,7,10-tetrazacyclododec-1-yl]acetate, gadolinium(3+). |
| 3-Gd | (1,3,5-tris-(N-(DO3A-acetamido)-N-methyl-4-amino-2-methylphenyl)-[1,3,5]tria-zinane-2,4,6-trione) |

Example 1a

DNP Preparation of Butyric Acid in the Presence of a Trityl Radical as DNP Agent Butyric acid (11.7 mg, 0.13 mmol) was placed into an Eppendorf tube and mixed with 9.0 mg of a glycerol solution containing 39 mM of Radical 1. This preparation was 7 M with respect to butyric acid. The preparation formed a glass upon rapid freezing in liquid nitrogen.

Example 1b

DNP Preparation of Butyric Anhydride in the Presence Of a Trityl Radical as DNP Agent Butyric anhydride (40 µl, 0.24 mmol) was added to an Eppendorf tube and mixed with 1 mg of Radical 3 in a total concentration of 15 mM. This preparation was 6.5 M with respect to butyric anhydride (which, upon hydrolysis provides a 13 M concentration in butyric acid molecules). This anhydride formed a glass upon rapid freezing without addition of glass-forming agents. In comparison to example is it was possible to make a preparation of butyric anhydride without addition of glass forming agent and with a concentration of butyric acid which is twice the concentration of preparation 1a.

Example 1c

DNP Preparation of Butyric Acetic Anhydride in the Presence of a Trityl Radical as DNP Agent Butyric acetic anhydride (36 µl, 0.28 mmol) was added to an Eppendorf tube and mixed with 0.85 mg of acid form of Radical 3 in a total concentration of 15 mM. This preparation was 7.5 M with respect to butyric acetic acid. This mixed anhydride formed a glass upon rapid freezing without addition of glass-forming agents. In comparison to example is it was possible to make a preparation of butyric acetic anhydride without addition of glass former agents: furthermore, a second active metabolic contrast agent (acetic acid) is obtained.

Example 1d

DNP Preparation of Butyric Ethylcarbonic Anhydride in the Presence of a Trityl Radical as DNP Agent (Prophetic)

Butyric ethylcarbonic anhydride is liquid at room temperature and forms a glass upon rapid freezing according to the procedure of example 1b, in the absence of a glass forming additive. In addition to the active metabolic contrast agents, hydrolysis of this precursor further provides a pH marker ($H_2CO_3$) and a MR contrast agent (ethanol).

Example 1e

DNP Hyperpolarization of Butyric Anhydride and Dissolution in the Presence of Strong Base for Hydrolysis The composition from example 1b (25 mg, 0.16 mmol) was transferred from the Eppendorf tube to a sample cup and the sample cup was inserted into a DNP polariser. The composition was hyperpolarised under DNP conditions at 1.2 K in a 3.35 T magnetic field under irradiation with microwave (93.915 GHz). The sample was hyperpolarized for 75 min.

The sample was dissolved in 4 ml water with added NaOH (50 µl of 12M solution). The pH of the dissolved sample was 12. The solution was collected directly into a 10 mm NMR tube and transferred to a 14.1 T magnet where a time series of 5 degree 1D 13C-NMR spectra were recorded with a total delay between the pulses of 1 s. The anhydride was quantitatively hydrolyzed (up to at least 95%) after 10 s. The butyric anhydride polarized well and was easily hydrolyzed to butyrate during the time of the experiment.

Example 1f

DNP Hyperpolarization of Butyric Acetic Anhydride and Dissolution in the Presence of Strong Base for Hydrolysis The composition from example is (33 mg, 0.25 mmol) was transferred from the Eppendorf tube to a sample cup and the sample cup was inserted into a DNP polariser. The composition was hyperpolarised under DNP conditions at 1.2 K in a 3.35 T magnetic field under irradiation with microwave (93.915 GHz). The sample was hyperpolarized for 90 min.

The sample was dissolved in 5 ml water with added NaOH (125 μl of 12M). The solution was collected directly into a 10 mm NMR tube and transferred to a 14.1 pH 12.8 and 50° C.) T magnet where a time series of 5 degree 1D 13C-NMR spectra were recorded with a total delay between the pulses of 1 s. The butyric acetic anhydride was quantitatively hydrolyzed up to at least 95%, after 10 s. The butyric acetic anhydride polarized well and was easily hydrolyzed to butyrate during the time of the experiment.

Example 2a

DNP Preparation of Li-Acetoacetate in the Presence of a Gd-Chelate as Paramagnetic Metal Ion and a Trityl Radical as DNP Agent Li-acetoacetate (22.4 mg, 0.21 mmol) was added to an Eppendorf tube and mixed with 28 μl of a DMSO preparation (25 mM Radical 3 and 0.8 mM 3-Gd). This preparation was 4 M with respect to Li-acetoacetate. The preparation formed a glass upon rapid freezing in liquid nitrogen.

Example 2b

DNP Preparation of Diketene in the Presence of a Gd-Chelate as Paramagnetic Metal Ion and a Trityl Radical as DNP Agent To an Eppendorf tube was added diketene (9.6 mg, 0.11 mmol) and mixed with 4.7 mg of a DMSO preparation of Radical 3 (45 mM) and 3-Gd (1.5 mM). This preparation was 8.5 M with respect to diketene. The preparation formed a glass upon rapid freezing in liquid nitrogen. In comparison to example 2a the concentration of acetoacetic acid is twice as high.

Example 2c

DNP Preparation of Ethyl Acetoacetate in the Presence of a Trityl Radical as DNP Agent Ethyl acetoacetate (45 μl, 0.34 mmol) was added to an Eppendorf tube and mixed with acid form of Radical 2 (0.7 mg, 0.65 μmol) in a total concentration of 15 mM. This preparation was 8 M with respect to ethyl acetoacetate. This ester formed a glass upon rapid freezing without addition of glass-forming agents. In comparison to example 2a it was possible to make a preparation of ethyl acetoacetate without addition of glass former agents and the concentration of ethylacetoacetate is twice as high.

Example 2d

DNP Hyperpolarization of Li-Acetoacetate and Dissolution in Phosphate Buffer

The entire composition from example 2a was transferred from the Eppendorf tube to a sample cup and the sample cup was inserted into a DNP polariser. The composition was hyperpolarised under DNP conditions at 1.2 K in a 3.35 T magnetic field under irradiation with microwave (93.915 GHz). The sample was hyperpolarized for 75 min.

The sample was dissolved in 5 ml phosphate buffer pH 7.3 (40 mM+EDTA).

pH 7.4 after dissolution. The solution was collected directly into a 10 mm NMR tube and transferred to a 14.1 T magnet where a 90 degree 1D 13C-NMR spectrum was recorded. Decarboxylation of acetoacetate into bicarbonate and acetone was detected. The amount of degradation was quantified to 40% with 1H NMR on a DNP sample following dissolution.

Example 2e

DNP Hyperpolarization of Diketene and Dissolution in the Presence of Strong Base for Hydrolysis The entire composition from example 2b was transferred from the Eppendorf tube to a sample cup and the sample cup was inserted into a DNP polariser. The composition was hyperpolarised under DNP conditions at 1.2 K in a 3.35 T magnetic field under irradiation with microwave (93.915 GHz). The sample was hyperpolarized for 3 hours.

The sample was dissolved in 5 ml water with added NaOH (125 μl of 12 M). The solution was collected directly into a 10 mm NMR tube and transferred to a 14.1 T magnet (pH 13) where a time series of 64 five degree 1D 13C-NMR spectra were recorded with a total delay between the pulses of 3 s. The lactone was quantitatively hydrolyzed up to at least 95%, after 10 s. The diketene polarized well and was easily hydrolyzed to acetoacetate during the time of the experiment. No substantial degradation (decarboxylation) of acetoacetate was observed. The T1 of the hydrolyzed product, acetoacetate is 32 s (14.1 T and 37° C.).

Example 2f

DNP Hyperpolarization of Ethyl Acetoacetate and Dissolution in the Presence of Strong Base for Hydrolysis The composition from example is (20.5 mg, 0.16 mmol) was transferred from the Eppendorf tube to a sample cup and the sample cup was inserted into a DNP polariser. The composition was hyperpolarised under DNP conditions at 1.2 K in a 3.35 T magnetic field under irradiation with microwave (93.915 GHz). The sample was hyperpolarized for 2 hours.

The sample was dissolved in 5 ml water with added NaOH (200 μl of 12 M). The solution was collected directly into a 10 mm NMR tube and transferred to a 14.1 T magnet (pH 12.8) where a time series of 5 degree 1D 13C-NMR spectra were recorded with a total delay between the pulses of 3 s. The ester was only partly hydrolyzed. The ester polarized well and was approximately 20% hydrolyzed to acetoacetate after 10 s. No substantial degradation (decarboxylation) was measured for the acetoacetate. The T1 of the C1 position in the hydrolyzed product, acetoacetate, is 32 s (14.1 T and 37° C.).

Example 2g

DNP Hyperpolarization of Ethyl Acetoacetate and Dissolution in the Presence of Esterase for Hydrolysis The composition from example 2c (13.2 mg, 0.1 mmol) was transferred from the Eppendorf tube to a sample cup and the sample cup was inserted into a DNP polariser. The composition was hyperpolarized under DNP conditions for 2 hours at 1.2 K in a 3.35 T magnetic field under irradiation with microwave (93.915 GHz).

The sample was dissolved in 5 ml 40 mM phosphate buffer pH 7.3+100 mg/l EDTA, thus resulting in an ester concentration of 20 mM. 1 ml of the ester solution was injected through a transfer line into a 10 mm NMR tube placed at 14.1 T and 37° C. The 10 mm NMR tube contained a 500 µl solution of approximately 270 U of a carboxylic-ester hydrolase from porcine liver. A time series of 10 degree 1D 13C-NMR spectra were recorded with a total delay between the pulses of 3 s. The ester was fully hydrolyzed to acetoacetate after 12s. No degradation (decarboxylation) was detected for the acetoacetate.

Example 3a

DNP Preparation of Cis-Aconitic Acid in the Presence of a Gd-Chelate as Paramagnetic Metal Ion and a Trityl Radical as DNP Agent Cis-aconitic acid (18.6 mg, 0.11 mmol) was added to an Eppendorf tube and mixed with a 32.5 µl DMSO preparation (25 mM Radical 3 and 0.8 mM 3-Gd). This preparation was 2.5 M with respect to cis-aconitic acid. The preparation formed a glass upon rapid freezing in liquid nitrogen.

Example 3b

DNP Preparation of Cis-Aconitic Anhydride in the Presence of a Gd-Chelate as Paramagnetic Metal Ion and a Trityl Radical as DNP Agent Cis-aconitic anhydride (188 mg, 1.2 mmol) was added to an Eppendorf tube and mixed with 2.85 mg (2 µmol) of Radical 1 and 0.98 mg of a 83 µmol/g solution of 3-Gd. This preparation was 9 M with respect to cis-aconitic anhydride. The melted preparation formed a glass upon rapid freezing without addition of glass-forming agents. In comparison to example 3a it was possible to make a preparation of cis-aconitic anhydride without addition of glassformer agents and the concentration of cis-aconitic acid is more than three times as high.

Example 3c

DNP Hyperpolarization of Cis-Aconitic Acid and Dissolution in the Presence of Base for Neutralization The entire composition from example 2a was transferred from the Eppendorf tube to a sample cup and the sample cup was inserted into a DNP polariser. The composition was hyperpolarised under DNP conditions at 1.2 K in a 3.35 T magnetic field under irradiation with microwave (93.915 GHz). The sample was hyperpolarized for 75 min.

The sample was dissolved in 5 ml phosphate buffer (40 mM, pH 7.3) with added 30 µl 12 M NaOH. The pH was 7.2 after dissolution. The solution was collected directly into a 10 mm NMR tube and transferred to a 14.1 T magnet where a time series of 5 degree 1D 13C-NMR spectra were recorded with a total delay between the pulses of 3 s. The presence of trans isomer of aconitate was detected, in an amount of about 10%.

Example 3d

DNP Hyperpolarization of Cis-Aconitic Anhydride and Dissolution in the Presence of Strong Base for Hydrolysis The composition from example 2b was melted on a water-bath and stirred with a magnetic stirrer. 45 mg of this preparation (0.29 mmol) was transferred from the Eppendorf tube to a sample cup and the sample cup was inserted into a DNP polariser. The composition was hyperpolarised under DNP conditions at 1.2 K in a 3.35 T magnetic field under irradiation with microwave (93.915 GHz). The sample was hyperpolarized for 90 min.

The sample was dissolved in 6 ml water with added NaOH (190 µl of 12 M). The solution was collected directly into a 10 mm NMR tube and transferred to a 14.1 T magnet (pH 12.8) where a time series of 64 five degree 1D 13C-NMR spectra were recorded with a total delay between the pulses of 3 s. The cis-aconitic anhydride was quantitatively hydrolyzed up to at least 95%, after 10s. The cis-aconitic anhydride polarized well and was easily hydrolyzed to cis-aconitate during the time of the experiment. The T1 of the hydrolyzed product, cis-aconitate is 24 s (14.1 T and 37° C.). In contrast to example 3b, the presence of trans-aconitate was neglectable.

Example 4a

DNP Preparation of Succinic Acid in the Presence of a Gd-Chelate as Paramagnetic Metal Ion and a Trityl Radical as DNP Agent Succinic acid (42.1 mg, 0.35 mmol) was added to an Eppendorf tube and mixed and mixed with 92 mg of a DMSO preparation (20 mM Radical 3 and 0.8 mM 3-Gd). This preparation was 4 M with respect to succinic acid. The preparation formed a glass upon rapid freezing in liquid nitrogen.

Example 4b

DNP Preparation of Succinic Anhydride in the Presence of a Gd-Chelate as Paramagnetic Metal Ion and a Trityl Radical as DNP Agent Succinic anhydride (21.5 mg, 0.21 mmol) was added to an Eppendorf tube and mixed with 21.8 mg of a DMSO solution of Radical 3 (30 mM) and of 3-Gd (1 mM). This preparation was 6 M with respect to succinic anhydride. This anhydride formed a glass upon rapid freezing. In comparison to example 4a it is possible to make a preparation of succinic anhydride in higher concentration.

Example 4c

DNP Hyperpolarization of Succinic Anhydride and Dissolution in the Presence of Strong Base for Hydrolysis The entire composition from example 4b was transferred from the Eppendorf tube to a sample cup and the sample cup was inserted into a DNP polariser. The composition was hyperpolarised under DNP conditions at 1.2 K in a 3.35 T magnetic field under irradiation with microwave (93.915 GHz). The sample was hyperpolarized for 60 min.

The sample was dissolved in 5 ml water with added NaOH (150 µl of 12 M). The solution was collected directly into a 10 mm NMR tube and transferred to a 14.1 T magnet (pH 12.8) where a time series of 5 degree 1D 13C-NMR spectra were recorded with a total delay between the pulses of 3 s. The anhydride was quantitatively hydrolyzed up to at least 95%, after 10 s. The succinic anhydride polarized well and was easily hydrolyzed to succinate during the time of the experiment. The T1 of the hydrolyzed product, succinate is 33 s (14.1 T and 37° C.).

Example 4d

DNP Preparation of succinic-(1)-ethyl ester in the Presence of a Gd-Chelate as Paramagnetic Metal Ion and a Trityl Radical as DNP Agent Succinic-(1)-ethyl ester (111 mg, 0.75 mmol) was added to an Eppendorf tube and mixed with the carboxylic acid form of Radical 2 (2.4 mg, 1.5 µmol) and 3-Gd (3.4 µl of a 14.5 mM solution in water). This preparation was 6 M with respect to succinic-(1)-ethyl ester. This ester formed a glass upon rapid freezing. In comparison to example 4a it is possible to make a preparation of succinic-(1)-ethyl ester in higher concentration and without additive.

Example 4e

DNP Hyperpolarization of succinic-(1)-ethyl ester and Dissolution in the Presence of Strong Base for Hydrolysis 45.4 mg of the composition from example 4c was transferred from the Eppendorf tube to a sample cup and the sample cup was inserted into a DNP polariser. The composition was hyperpolarized under DNP conditions for 60 min at 1.2 K in a 3.35 T magnetic field under irradiation with microwave (93.900 GHz).

The sample was dissolved in 6 ml water with added NaOH (195 µl of 12 M). The solution was collected directly into a 10 mm NMR tube and transferred to a 14.1 T magnet (pH 13) where a time series of 5 degree 1D 13C-NMR spectra were recorded with a total delay between the pulses of 3 s. The ester was hydrolyzed up to at least 95%, after 20 s.

Example 5a

DNP Preparation of L-Glutamine in the Presence of Sodium Hydroxide, a Gd-Chelate as Paramagnetic Metal Ion and a Trityl Radical as DNP Agent L-Glutamine (50.9 mg, 0.35 mmol) was added to an Eppendorf tube and dissolved in 29 µl of 12 M NaOH and mixed with 1.7 mg of radical 1 and 3-Gd (2.3 µl of a 14.5 mM water stock solution). This preparation was 4 M with respect to L-glutamine. The preparation formed a glass upon rapid freezing in liquid nitrogen. L-Glutamine is an unstable compound under the DNP preparation conditions. The amount of degradation was quantified to 14% with 1H NMR on the solubilised described DNP sample.

Example 5b

DNP Preparation of N-acetyl-L-glutamine in the Presence of Sodium Hydroxide, a Gd-Chelate as Paramagnetic Metal Ion and a Trityl Radical as DNP Agent N-acetyl-L-glutamine (57.2 mg, 0.3 mmol) was added to an Eppendorf tube and dissolved in 25.3 µl of 12 M NaOH and mixed with 1.9 mg of radical 1 and 3-Gd (2.3 µl of a 14.5 mM water stock solution). The preparation formed a glass upon rapid freezing in liquid nitrogen. This preparation compared to example 5a hold a slightly higher concentration 4.5 M with respect to N-acetyl-L-glutamine and N-acetyl glutamine does not degrade in the DNP preparation as measured with 1H NMR on the solubilised described DNP sample.

Example 5c

DNP Hyperpolarization of N-acetyl-L-glutamine, Dissolution and Addition of N-Acetylase for Hydrolysis 94.5 mg of the composition from example 5b was transferred from the Eppendorf tube to a sample cup and the sample cup was inserted into a DNP polariser. The composition was hyperpolarised under DNP conditions at 1.2 K in a 3.35 T magnetic field under irradiation with microwave (93.900 GHz). The sample was hyperpolarized for 60 min.

The sample was dissolved in 5 ml 40 mM phosphate buffer (40 mM, pH 7.3). 500 µl of the hyperpolarized N-acetyl-L-glutamine solution was injected through a transfer line into a 10 mm NMR tube placed at 14.1 T and 37° C. The 10 mm NMR tube contained a 1 ml phosphate solution of approximately 90 U of an acylase from porcine kidney. A time series of 5 degrees 1D 13C-NMR spectra were recorded with a total delay between the pulses of 3 s.

The N-acetyl-L-glutamine was fully hydrolyzed after 45 s. The degradation of L-glutamine (a tendency of L-glutamine to form an unwanted cyclic form, pyroglutamate), is heat and acid induced and is accentuated in the dissolution process (high temperature and addition of acid to neutralize the basic preparation). N-acetyl-L-glutamine does not degrade in the dissolution process.

Example 6a

DNP Preparation of 2-13C-d2-glycine in the Presence of Sodium Hydroxide, a Gd-Chelate as Paramagnetic Metal Ion and a Trityl Radical as DNP Agent 2-13C-d2-Glycine (19.3 mg, 0.25 mmol) was added to an Eppendorf tube and dissolved in 16 µl of 12 M NaOH and mixed with 4 mg of a NaOH solution of radical 1 (100 µmol/g) and Gadoteridol (10 µmol/g) This preparation is 7 M with respect to glycine. The preparation forms a glass upon rapid freezing in liquid nitrogen.

Example 6b

DNP Preparation of 2-13C-d2-N-acetyl glycine in the Presence of Sodium Hydroxide, a Gd-Chelate as Paramagnetic Metal Ion and a Trityl Radical as DNP Agent 2-13C-d2-N-acetyl glycine (30.7 mg, 0.255 mmol) was added to an Eppendorf tube and dissolved in 22 µl of a 12 M NaOH solution (73 µl, 100 mg) of radical 1 (3.4 mg, 2.4 µmol) and Gadoteridol (2.5 mg of 100 µmol/g solution). This preparation compared to example 6a holds a lower concentration 5.5 M with respect to N-acetyl glycine. The preparation formed a glass upon rapid freezing in liquid nitrogen.

Example 6c

DNP Hyperpolarization of 2-13C-d2-glycine and Dissolution in the Presence of Strong Acid for Neutralization The composition from example 6a was hyperpolarized with DNP conditions for 60 min at 1.2 K in a 3.35 T magnetic field under irradiation with microwave (93.900 GHz).

The sample was dissolved in 5 ml phosphate buffer (100 mM, pH 7) with added one equivalent HCl. The pH is 7.1 after dissolution. The solution was collected directly into a 10 mm NMR tube and transferred to a 14.1 T magnet where a time series of 3 degree 1D 13C-NMR spectra were recorded with a total delay between the pulses of 3 s.

The solid state signal was 280 (area in arbitrary units divided by mmol 13C) and the liquid state polarization was 12.5% with a high field liquid state T1 of 46 s.

Example 6d

DNP Hyperpolarization of 2-13C-d2-N-acetyl glycine and Dissolution

The composition from example 6b was hyperpolarized with DNP conditions for 60 min at 1.2 K in a 3.35 T magnetic field under irradiation with microwave (93.900 GHz).

The sample was dissolved in 5 ml phosphate buffer (40 mM, pH 7.3). The pH is 7.2 after dissolution. The solution was collected directly into a 10 mm NMR tube and transferred to a 14.1 T magnet where a time series of 3 degree 1D 13C-NMR spectra were recorded with a total delay between the pulses of 3 s.

The solid state signal was 376 (area in arbitrary units divided by mmol 13C) and the liquid state polarization was 21% with a high field liquid state T1 of 40 s.

Compared to example 6c higher solid-state signal was obtained and a dissolution without loss of polarization and higher liquid state polarization was obtained.

Example 6e

DNP Hyperpolarization of N-Acetyl Glycine and Dissolution Following which the Presence of N-Acetylase for Hydrolysis 35 mg of N-acetyl glycine (117.1 g/mol, 0.298 mmol) was dissolved in 26 µl 12 M NaOH. Heating, sonication and vortexing was applied to create a clear glassing solution. The total weight of the sample was 71 mg (50 µl weigh 65 mg). 1.05 mg Radical 1 and 1.5 µl of a 3-Gd stock solution (14.5 mmol/g) was added. The total N-acetyl glycine concentration in the sample was 5.5 M, the radical concentration was 13.5 mM, and the 3-Gd concentration was 0.4 mM.

35.8 mg of the composition was transferred from the Eppendorf tube to a sample cup and the sample cup was inserted into a DNP polariser. The composition was hyperpolarized under DNP conditions for 60 min at 1.2 K in a 3.35 T magnetic field under irradiation with microwave (93.900 GHz).

The sample was dissolved in 7 ml 40 mM phosphate buffer (40 mM, pH 7.3). 1 ml of the hyperpolarized N-acetyl glycine solution was injected through a transfer line into a 10 mm NMR tube placed at 14.1 T and 37° C. The 10 mm NMR tube contained a 500 µl phosphate solution of approximately 230 U of an acylase (5.2 mg) from porcine kidney. A time series of 5 degrees 1D 13C-NMR spectra was recorded with a total delay between the pulses of 3 s.

The N-acetyl glycine was fully hydrolyzed after 30 s.

Example 7a

DNP Preparation of 2-oxoglutarate Disodium Salt in the Presence of a Gd-Chelate as Paramagnetic Metal Ion and a Trityl Radical as DNP Agent 2-oxoglutarate sodium salt (137 mg, 0.61 mmol) was dissolved in 100 µl heated water. 2.06 mg Radical 1 was weighed into an Eppendorf tube and 111 µl of the 2-oxoglutarate/water solution was added resulting in a total sample amount of 143 mg). To this sample 2.7 mg of a 14.5 µmol/g stock solution of 3-Gd was added. The preparation was gently heated and whirl-mixed to dissolution. This preparation was 3.4 M with respect to 2-oxoglutarate. The preparation formed a glass upon rapid freezing in liquid nitrogen.

Example 7b

DNP Preparation of 2-oxoglutaric-(1)-ethyl ester in the Presence of a Gd-Chelate as Paramagnetic Metal Ion and a Trityl Radical as DNP Agent 2-oxoglutaric-(1)-ethyl ester (31 mg, 0.18 mmol) was added to an Eppendorf tube and mixed with 0.7 mg (0.45 µmol) of radical 3. This preparation was 6.5 M with respect to 2-oxoglutarate. This ethyl ester formed a glass upon rapid freezing. In comparison to example 7a it is possible to make a preparation of 2-oxoglutaric-(1)-ethyl ester in higher concentration.

Example 7c

DNP Hyperpolarization of 2-oxoglutaric-(1)-ethyl ester and Dissolution in the Presence of Strong Base for Hydrolysis 31 mg of the composition from example 7b was transferred from the Eppendorf tube to a sample cup and the sample cup was inserted into a DNP polariser. The composition was hyperpolarised under DNP conditions at 1.2 K in a 3.35 T magnetic field under irradiation with microwave (93.900 GHz). The sample was hyperpolarized for 90 min.

The sample was dissolved in 6 ml $D_2O$ with added NaOD (35 µl of 10 M). The solution was collected directly into a 10 mm NMR tube and transferred to a 14.1 T magnet (pH 11) where a time series of 5 degree 1D 13C-NMR spectra were recorded with a total delay between the pulses of 3 s. The ester was hydrolyzed up to at least 95%, after 15 s. The 2-oxoglutaric-(1)-ethyl ester was easily hydrolyzed to 2-oxoglutarate during the time of the experiment.

Example 8a

DNP Preparation of Malic Acid in the Presence of a Trityl Radical as DNP Agent

Malic acid (49 mg, 0.365 mmol) was dissolved in 100 mg of a DMSO stock solution (320 mg DMSO with 8.6 mg (5.4 µmol) of radical 3). This preparation was 4 M with respect to malic acid. The preparation formed a glass upon rapid freezing in liquid nitrogen.

Example 8b

DNP Preparation of malic-(1)-ethyl ester in the Presence of a Trityl Radical as DNP Agent Malic-(1)-ethyl ester (108 mg, 0.66 mmol) was added to an Eppendorf tube and mixed with 1.7 mg (1.1 µmol) of radical 3. This preparation was 7.4 M with respect to malate. This ethyl ester formed a glass upon rapid freezing. In comparison to example 8a it is possible to make a preparation of malic-(1)-ethyl ester in higher concentration and without additive.

Example 8c

DNP Hyperpolarization of malic-(1)-ethyl ester and Dissolution in the Presence of Strong Base for Hydrolysis 39.9 mg of the composition from example 8b was transferred from the Eppendorf tube to a sample cup and the sample cup was inserted into a DNP polariser. The composition was hyperpolarised under DNP conditions at 1.2 K in a 3.35 T magnetic field under irradiation with microwave (93.900 GHz). The sample was hyperpolarized for 80 min.

The sample was dissolved in 6 ml water with added NaOH (92 µl of 12 M). The solution was collected directly into a 10 mm NMR tube and transferred to a 14.1 T magnet (pH 12.9) where a time series of 5 degree 1D 13C-NMR spectra were recorded with a total delay between the pulses of 3 s. The ester was hydrolyzed up to at least 95%, after 20 s. The malic-(1)-ethyl ester was easily hydrolyzed to malate during the time of the experiment.

Example 9a

DNP Preparation of L-Phenylalanine in the Presence of a Trityl Radical as DNP Agent L-Phenylalanine (126.3 mg, 0.76 mmol) was dissolved in 69.5 µl 12 M NaOH+69.5 µl water. This solution was mixed with 4.6 mg (3.2 µmol) radical 1. This preparation was 3.5 M with respect to L-phenylalanine. The preparation formed a glass upon rapid freezing in liquid nitrogen.

Example 9b

DNP Preparation of Ethyl Phenylalanine in the Presence of a Trityl Radical as DNP Agent Ethyl phenylalanine (49 mg, 0.25 mmol) was added to an Eppendorf tube and mixed with 1.2 mg (0.78 µmol) of radical 3. This preparation was 5.5 M with respect to phenylalanine. This ethyl ester formed a glass upon rapid freezing. In comparison to example 9a it is possible to make a preparation of ethyl phenylalanine in higher concentration.

Example 9c

DNP Hyperpolarization of Ethyl Phenylalanine and Dissolution in the Presence of Strong Base for Hydrolysis 49 mg of the composition from example 9b was transferred from the Eppendorf tube to a sample cup and the sample cup was inserted into a DNP polariser. The composition was hyperpolarised under DNP conditions at 1.2 K in a 3.35 T magnetic field under irradiation with microwave (93.900 GHz). The sample was hyperpolarized for 60 min.

The sample was dissolved in 7 ml water with added NaOH (83 µl of 12 M). The solution was collected directly into a 10 mm NMR tube and transferred to a 14.1 T magnet (pH 12.2) where a time series of 5 degree 1D 13C-NMR spectra were recorded with a total delay between the pulses of 3 s. The ester was hydrolyzed up to at least 95%, after 15 s. The ethyl phenylalanine was easily hydrolyzed to phenylalanine during the time of the experiment.

Example 10a

DNP Hyperpolarization of 1-13C-pyroglutamate in the Presence of a Trityl Radical as DNP Agent 1-13C Pyroglutamic acid (35.9 mg, 0.276 mmol) was mixed with 24 µl 12 M NaOH. To this solution 1.1 mg (0.77 µmol) radical 1 was added. This preparation was 5.5 M with respect to pyroglutamate. The preparation formed a glass upon rapid freezing in liquid nitrogen. This entire sample was hyperpolarized under DNP conditions at 1.2 K in a 3.35 T magnetic field under irradiation with microwave (93.900 GHz) until the polarization was fully build-up. The polarization was monitored in solid state with small pulse angles (5 degree) collected every 300 s. The polarization build-up time constant was calculated to be 2000 s. and the solid-state signal was 75 (area in arbitrary units divided by mmol 13C).

Example 10b

DNP Polarization of 1-13C-pyroglutamic ethyl ester in the Presence of a Trityl Radical as DNP Agent 1-13C pyroglutamic ethyl ester (61.3 mg, 0.387 mmol) was mixed with 0.71 mg (0.46 µmol) radical 3. This preparation was 7.5 M with respect to ethyl pyroglutamate. The preparation formed a glass upon rapid freezing in liquid nitrogen. This entire sample was polarized under DNP conditions at 1.2 K in a 3.35 T magnetic field under irradiation with microwave (93.900 GHz) until the polarization was fully built-up. The polarization was monitored in solid state with small pulse angles (5 degree) collected every 300 s. The polarization build-up time constant was calculated to be 2070 s. and the solid-state polarization was 350 (area in arbitrary units divided by mmol 13C). In comparison to example 10a it is possible to make a preparation of pyroglutamate ethyl ester in higher concentration, the ethyl pyroglutamate polarizes more than 4.5 times as well as the pyroglutamate with the same polarization build-up time constant and with a lower radical concentration in the sample.

Example 10c

Dissolution of DNP Hyperpolarized Ethyl Pyroglutamate in the Presence of Strong Base for Hydrolysis 36.8 mg of the composition from example 10b was transferred to a sample cup and the sample cup was inserted into a DNP polariser. The composition was hyperpolarised under DNP conditions at 1.2 K in a 3.35 T magnetic field under irradiation with microwave (93.900 GHz). The sample was hyperpolarized for 60 min.

The sample was dissolved in 5 ml water with added NaOH (95 μl of 12 M). The solution was collected directly into a 10 mm NMR tube and transferred to a 14.1 T magnet (pH 11) where a time series of 5 degree 1D 13C-NMR spectra were recorded with a total delay between the pulses of 3 s. The ester was hydrolyzed up to at least 95%, in less than 10 s. The ethylpyroglutamate was easily hydrolyzed to pyroglutamate during the time of the experiment.

Example 11a

DNP Polarization of 1-13C-L-oxothiazolidine-4-carboxylic acid (OTZ) in the Presence of a Trityl Radical as DNP Agent 1-13C OTZ (36 mg, 0.24 mmol) was mixed with 21 μl 12 M NaOH. To this solution 0.77 mg (0.54 μmol) radical 1 was added. This preparation was 4 M with respect to OTZ. The preparation formed a glass upon rapid freezing in liquid nitrogen. This entire sample was polarized under DNP conditions at 1.2 K in a 3.35 T magnetic field under irradiation with microwave (93.900 GHz) until the polarization was fully built-up. The polarization was monitored in solid state with small pulse angles (5 degree) collected every 300 s. The polarization build-up time constant was calculated to be 3500 s. and the solid-state signal was 305 (area in arbitrary units divided by mmol 13C).

Example 11b

DNP Polarization of 1-13C-OTZ ethyl ester in the Presence of a Trityl Radical as DNP Agent 1-13C OTZ ethyl ester (84.8 mg, 0.48 mmol) was mixed with 0.98 mg (0.94 μmol) radical 2 to make a solution containing 14 mM radical called solution A. To 22.1 mg (0.125 mmol) of solution A and additional amount of 1-13C OTZ ethyl ester (6 mg, 0.034 mmol) was added to make a radical concentration of 11 mM. This preparation was 7 M with respect to OTZ ethyl ester. The preparation formed a glass upon rapid freezing in liquid nitrogen. This entire sample was polarized under DNP conditions at 1.2 K in a 3.35 T magnetic field under irradiation with microwave (93.900 GHz) until the polarization was fully built-up. The polarization was monitored in solid state with small pulse angles (5 degree) collected every 300 s. The polarization build-up time constant was calculated to be 1925 s. and the solid-state signal was 380 (area in arbitrary units divided by mmol 13C).

In comparison to example 11a it is possible to make a preparation of OTZ ethyl ester in higher concentration, the OTZ ester polarizes 1.2 times as well as OTZ with the same polarization build-up time constant and with a lower radical concentration in the sample.

Example 11c

Dissolution of DNP Hyperpolarized Ethyl OTZ in the Presence of Strong Base for Hydrolysis Ethyl OTZ (78.4 mg, 0.448 mmol) was mixed with 1.49 mg (0.97 μmol) radical 3 was transferred to a sample cup and the sample cup was inserted into a DNP polariser. The composition was hyperpolarised under DNP conditions at 1.2 K in a 3.35 T magnetic field under irradiation with microwave (93.900 GHz). The sample was hyperpolarized for 60 min.

The sample was dissolved in 5 ml water with added NaOH (73 μl of 12 M). The solution was collected directly into a 10 mm NMR tube and transferred to a 14.1 T magnet (pH 12.6) where a time series of 5 degree 1D 13C-NMR spectra were recorded with a total delay between the pulses of 3 s. The ester was hydrolyzed up to at least 95%, in less than 10 s. The ethyl OTZ was easily hydrolyzed to OTZ during the time of the experiment.

Example 12a

DNP Hyperpolarization of 1-13C-Itaconic Acid in the Presence of a Trityl Radical as DNP Agent 1-13C Itaconic acid (39.7 mg, 0.3 mmol) was mixed with 51.1 mg 12 M NaOH. To this solution 1.65 mg (1.15 μmol) radical 1 was added. This preparation was 4.5 M with respect to Itaconic acid. The preparation formed a glass upon rapid freezing in liquid nitrogen. This entire sample was polarized under DNP conditions at 1.2 K in a 3.35 T magnetic field under irradiation with microwave (93.900 GHz) until the polarization was fully built-up. The polarization was monitored in solid state with small pulse angles (5 degree) collected every 300 s. The polarization build-up time constant was calculated to be 1790 s. and the solid-state signal was 150 (area in arbitrary units divided by mmol 13C).

Example 12b

DNP Hyperpolarization of 1-13C-Itaconate Diethyl Ester in the Presence of a Trityl Radical as DNP Agent 1-13C Itaconate diethyl ester (127.9 mg, 0.686 mmol) was mixed with 1.5 mg (1 μmol) radical 3. This preparation was 5.6 M with respect to itaconate diethyl ester. The preparation formed a glass upon rapid freezing in liquid nitrogen. 63.2 mg (0.33 mmol) of this sample was hyperpolarized under DNP conditions at 1.2 K in a 3.35 T magnetic field under irradiation with microwave (93.900 GHz) until the polarization was fully built-up. The polarization was monitored in solid state with small pulse angles (5 degree) collected every 300 s. The polarization build-up time constant was calculated to be 2120s. and the solid-state signal was 340 (area in arbitrary units divided by mmol 13C). In comparison to example 12a it is possible to make a preparation of in higher concentration, the itaconate ethyl ester polarizes 2.3 times as well as the Itaconate with similar polarization build-up time constant.

The invention claimed is:

1. A process for preparing and using, a hyperpolarized active substrate in a method of magnetic resonance investigation, which comprises the steps of
   a) preparing a hyperpolarized precursor of said substrate by dynamic nuclear polarisation (DNP) methods;
   b) contacting said precursor with an aqueous carrier to transform it into said hyperpolarized active substrate, wherein the transformation is effected b hydrolysis of the precursor, and wherein the hydrolysis provides a transformation of at least 50% of the recursor into the active substrate;
   c) administering the active substrate to a subject;
   d) submitting the subject to a radiation frequency selected to excite nuclear spin transitions in a non-zero nuclear spin nuclei of the active substrate or of a metabolite thereof; and
   e) recording a MR signal from said excited nuclei,
   wherein said precursor is selected from the group consisting of organic cyclic anhydrides, organic linear anhydrides, cyclic diketenes, acyclic diketenes, esters, lactones and amides.

2. The process according to claim 1, wherein said hydrolysis provides a transformation of at least 75% of the precursor.

3. The process according to claim 1, wherein said precursor is enriched with one or more respective non-zero nuclear spin nuclei, selected from the group consisting of 13C, 19F and 15N nuclei.

4. The process according to any one of claim 1 or 3, wherein said precursor is selected from the group consisting of: butyric anhydride, butyric-acetic anhydride, cis-aconitic anhydride, 4-methylideneoxetan-2-one, ethyl acetotacetate, succinic mono ethyl ester, succinic di ethyl ester, ethylpyroglutamate, dimethylglycine ethyl ester, 2-oxothiazolidine-4-carboxylic ethyl ester, 2-oxoulutaric mono ethyl ester, 2-oxoulutaric di ethyl ester, malic mono ethyl ester, malic di-ethyl ester, phenylalanine ethyl ester, N-acetylglutamine and N-acetyl glycine.

5. The process according to claim 4, wherein said precursor is selected from the group consisting, of: 1,1'-13C2-butyric anhydride, 1-13C-butyric-acetic anhydride, 6-13C-cis-aconitic anhydride, 4-methylideneoxetan-2-13C-one, 1-13C-ethyl acetotacetate, 1,3-13C2-ethyl acetotacetate, 1,4-13C2-succinate-(1)-ethyl ester, 1-13C-ethylpyroglutamate, 2-13C-d2-dimethylglycine ethyl ester, 1-13C-ethyl 2-oxothiazolidine-4-carboxylate, 1-13C-2-oxoglutaratet 1 lethyl ester, 1,4-13C2-ethylmate, 5-13C-N-acetylglutamine and 2-13C-2d-N-acetyl glycine.

6. The process according to claim 1, wherein the aqueous carrier is selected from the group consisting: water, physiological saline solutions and buffer solutions.

7. The process according to claim 6, wherein the aqueous carrier further comprises an additive selected from the group consisting of: alkaline base, organic acid, and inorganic acid.

8. The process according to claim 7, wherein said additive is selected from the group consisting of: sodium hydroxide and hydrochloric acid.

9. The process according to claim 1, wherein the transformation of the hyperpolarized precursor is carried out in the presence of an enzyme.

10. The process of claim 9, wherein said enzyme is selected from the group consisting of esterases, acylases and lipases.

11. The process according to claim 1, wherein the precursor is an ester that presents liquid below 100° C. and forms non crystalline solids when rapidly frozen.

12. The process according to claim 11, wherein said ester is selected from the group consisting of ethylacetoacetate, ethylpyroglutamate, 2-oxothiazolidine-4-carboxylic ethyl ester, and dimethyiglycine ethyl ester, succinic-(1)-ethyl ester, 2-oxoglutaric-(1)-ethyl ester, malic-(1)-ethyl ester, and phenylalanine ethyl ester.

13. The process according to claim 3, wherein said precursor is deuterated.

14. The process according to claim 11, wherein the process for preparing a hyperpolarized active substrate is carried out in the presence of an enzyme.

* * * * *

UNITED STATES PATENT AND TRADEMARK OFFICE
CERTIFICATE OF CORRECTION

PATENT NO. : 9,694,090 B2
APPLICATION NO. : 13/639682
DATED : July 4, 2017
INVENTOR(S) : Silvio Aime et al.

It is certified that error appears in the above-identified patent and that said Letters Patent is hereby corrected as shown below:

In the Claims

Claim 1, Column 39, Line 2 reads "and using, a" and should read --and using a--; Line 4 reads "comprises the steps of" and should read --comprises the steps of:--; Line 9 reads "effected b hydrolysis" and should read --effected by hydrolysis--; Line 11 reads "the recursor into" and should read --the precursor into--.

Column 40, Line 22, cancel the text beginning with "10. The process of claim 9" to and ending with "and phenylalanine ethyl ester." in Column 40, Line 33, and insert the following claims:

--10. The process of claim 9, wherein said enzyme is selected from the group consisting of: esterases, acylases and lipases.

11. The process according to claim 1, wherein the precursor is an ester that presents liquid below 100° C. and forms non crystalline solids when rapidly frozen.

12. The process according to claim 11, wherein said ester is selected from the group consisting of: ethylacetoacetate, ethylpyroglutamate, 2-oxothiazolidine-4-carboxylic ethyl ester, dimethylglycine ethyl ester, succinic-(1)-ethyl ester, 2-oxoglutaric-(1)-ethyl ester, malic-(1)-ethyl ester, and phenylalanine ethyl ester.--.

Signed and Sealed this
Twenty-fifth Day of September, 2018

Andrei Iancu
*Director of the United States Patent and Trademark Office*